United States Patent
Ackermann et al.

(10) Patent No.: US 12,268,865 B2
(45) Date of Patent: Apr. 8, 2025

(54) CURRENT BIAS AS A CONTROL MECHANISM FOR ELECTRODE OPERATION

(71) Applicant: Presidio Medical, Inc., South San Francisco, CA (US)

(72) Inventors: Douglas Michael Ackermann, Reno, NV (US); Michael A. Faltys, San Francisco, CA (US); James Harris, San Francisco, CA (US); Kenneth S. Wu, San Francisco, CA (US)

(73) Assignee: Presidio Medical, Inc., San Mateo, CA (US)

( * ) Notice: Subject to any disclaimer, the term of this patent is extended or adjusted under 35 U.S.C. 154(b) by 514 days.

(21) Appl. No.: 17/779,006

(22) PCT Filed: Nov. 24, 2020

(86) PCT No.: PCT/US2020/062068
§ 371 (c)(1),
(2) Date: May 23, 2022

(87) PCT Pub. No.: WO2021/102447
PCT Pub. Date: Aug. 27, 2021

(65) Prior Publication Data
US 2023/0008440 A1    Jan. 12, 2023

Related U.S. Application Data

(60) Provisional application No. 62/939,659, filed on Nov. 24, 2019.

(51) Int. Cl.
*A61N 1/05* (2006.01)
*A61N 1/04* (2006.01)

(52) U.S. Cl.
CPC ............. *A61N 1/05* (2013.01); *A61N 1/0404* (2013.01)

(58) Field of Classification Search
None
See application file for complete search history.

(56) References Cited

U.S. PATENT DOCUMENTS

| 4,057,069 A | 11/1977 | Dorffer et al. |
| 4,917,093 A | 4/1990 | Dufresne et al. |

(Continued)

FOREIGN PATENT DOCUMENTS

| DE | 4324185 | 1/1995 |
| EP | 0 281 717 | 9/1988 |

(Continued)

OTHER PUBLICATIONS

Extended European Search Report dated Oct. 11, 2023 in Application No. 20889687.8 in 6 pages.

(Continued)

*Primary Examiner* — Erica S Lee
(74) *Attorney, Agent, or Firm* — KNOBBE, MARTENS, OLSON & BEAR, LLP

(57) ABSTRACT

Disclosed herein are systems and methods for electrically modulating tissue. Systems can include a current generator; at least one implantable working electrode, the at least one implantable working electrode configured to be in electrical communication with the current generator; at least one indifferent electrode; and a controller configured to signal the current generator to: generate a set of currents with a set of initial polarities to be delivered to the working electrodes; and wherein the at least one indifferent electrode absorbs a bias current which is equal in magnitude and opposite in polarity to a summation of the set of currents.

20 Claims, 13 Drawing Sheets

(56) References Cited

U.S. PATENT DOCUMENTS

| | | |
|---|---|---|
| 5,034,589 A | 7/1991 | Evans et al. |
| 5,833,714 A | 11/1998 | Loeb |
| 5,868,743 A | 2/1999 | Saul et al. |
| 6,139,545 A | 10/2000 | Utley et al. |
| 6,189,536 B1 | 2/2001 | Martinez et al. |
| 6,192,279 B1 | 2/2001 | Barreras et al. |
| 6,205,359 B1 | 3/2001 | Bovega |
| 6,293,266 B1 | 9/2001 | Oetting |
| 6,366,813 B1 | 4/2002 | DiLorenzo |
| 6,600,956 B2 | 7/2003 | Maschino et al. |
| 6,671,561 B1 | 12/2003 | Moaddeb |
| 6,819,956 B2 | 11/2004 | DiLorenzo |
| 6,895,280 B2 | 5/2005 | Meadows et al. |
| 6,907,295 B2 | 6/2005 | Gross et al. |
| 6,937,893 B2 | 8/2005 | Danz et al. |
| 6,974,533 B2 | 12/2005 | Zhou |
| 6,975,907 B2 | 12/2005 | Zanakis et al. |
| 7,079,903 B2 | 7/2006 | O'Brien |
| 7,216,001 B2 | 5/2007 | Hacket et al. |
| 7,421,299 B2 | 9/2008 | Frericks et al. |
| 7,428,438 B2 | 9/2008 | Parramon et al. |
| 7,437,193 B2 | 10/2008 | Parramon et al. |
| 7,502,652 B2 | 3/2009 | Gaunt et al. |
| 7,587,241 B2 | 9/2009 | Parramon et al. |
| 7,638,032 B2 | 12/2009 | Zhou et al. |
| 7,691,252 B2 | 4/2010 | Zhou et al. |
| 7,780,833 B2 | 8/2010 | Hawkins et al. |
| 7,881,808 B2 | 2/2011 | Borgaonkar et al. |
| 7,891,085 B1 | 2/2011 | Kuzma et al. |
| 7,909,764 B1 | 3/2011 | Wenzel et al. |
| 8,019,439 B2 | 9/2011 | Kuzma et al. |
| 8,034,229 B2 | 10/2011 | Zhou et al. |
| 8,121,703 B1 | 2/2012 | Palmer |
| 8,135,478 B2 | 3/2012 | Gross |
| 8,271,098 B2 | 9/2012 | Swanson et al. |
| 8,359,102 B2 | 1/2013 | Alataris et al. |
| 8,406,886 B2 | 3/2013 | Gaunt et al. |
| 8,417,352 B2 | 4/2013 | Carroll et al. |
| 8,509,903 B2 | 8/2013 | York et al. |
| 8,644,933 B2 | 2/2014 | Ozawa et al. |
| 8,646,172 B2 | 2/2014 | Kuzma et al. |
| 8,650,747 B2 | 2/2014 | Kuzma et al. |
| 8,712,533 B2 | 4/2014 | Alataris et al. |
| 8,768,472 B2 | 7/2014 | Fang et al. |
| 8,792,988 B2 | 7/2014 | Alataris et al. |
| 8,897,895 B2 | 11/2014 | Mashiach |
| 8,948,881 B2 | 2/2015 | Fisk |
| 8,983,614 B2 | 3/2015 | Kilgore et al. |
| 9,008,780 B2 | 4/2015 | Nudo et al. |
| 9,008,781 B2 | 4/2015 | Ahmed |
| 9,008,800 B2 | 4/2015 | Ackermann et al. |
| 9,011,310 B2 | 4/2015 | Ahmed |
| 9,037,248 B2 | 5/2015 | Durand et al. |
| 9,072,886 B2 | 7/2015 | Gaunt et al. |
| 9,119,966 B2 | 9/2015 | Franke et al. |
| 9,205,265 B2 | 12/2015 | Franke |
| 9,283,391 B2 | 3/2016 | Ahmed |
| 9,327,125 B2 | 5/2016 | Alataris et al. |
| 9,333,356 B2 | 5/2016 | Franke et al. |
| 9,333,357 B2 | 5/2016 | Alataris et al. |
| 9,364,661 B2 | 6/2016 | Kilgore et al. |
| 9,370,664 B2 | 6/2016 | Marnfeldt et al. |
| 9,381,350 B2 | 7/2016 | Ahmed |
| 9,384,990 B2 | 7/2016 | Musa |
| 9,387,322 B2 | 7/2016 | Bhadra et al. |
| 9,393,423 B2 | 7/2016 | Parramon et al. |
| 9,403,014 B2 | 8/2016 | Kilgore et al. |
| 9,480,842 B2 | 11/2016 | Alataris et al. |
| 9,492,665 B2 | 11/2016 | Khalil et al. |
| 9,498,621 B2 | 11/2016 | Ackermann et al. |
| 9,572,979 B2 | 2/2017 | Fridman et al. |
| 9,694,181 B2 | 7/2017 | Bhadra et al. |
| 9,707,390 B2 | 7/2017 | Ahmed |
| 9,707,391 B2 | 7/2017 | Ahmed |
| 9,782,593 B2 | 10/2017 | Parramon et al. |
| 9,789,329 B2 | 10/2017 | Ahmed |
| 9,821,157 B2 | 11/2017 | Ahmed et al. |
| 9,844,668 B2 | 12/2017 | Ahmed |
| 9,889,291 B2 | 2/2018 | Bhadra et al. |
| 10,071,241 B2 | 9/2018 | Bhadra et al. |
| 10,195,434 B2 | 2/2019 | Bhadra et al. |
| 10,272,240 B2 | 4/2019 | Ackermann et al. |
| 10,441,782 B2 | 10/2019 | Bhadra et al. |
| 11,027,126 B2 | 6/2021 | Ackermann et al. |
| 2002/0015963 A1 | 2/2002 | Keer |
| 2003/0040785 A1 | 2/2003 | Maschino et al. |
| 2004/0181261 A1 | 9/2004 | Manne |
| 2004/0215285 A1 | 10/2004 | Pollock |
| 2005/0075709 A1 | 4/2005 | Brennen et al. |
| 2006/0085048 A1 | 4/2006 | Cory et al. |
| 2006/0095088 A1 | 5/2006 | Ridder |
| 2006/0167527 A1 | 7/2006 | Femano et al. |
| 2006/0184211 A1 | 8/2006 | Gaunt et al. |
| 2006/0265027 A1 | 11/2006 | Vaingast et al. |
| 2007/0027490 A1 | 2/2007 | Ben-Haim et al. |
| 2007/0043400 A1 | 2/2007 | Donders et al. |
| 2007/0060815 A1 | 3/2007 | Martin et al. |
| 2007/0073354 A1 | 3/2007 | Knudson et al. |
| 2007/0083193 A1 | 4/2007 | Werneth et al. |
| 2007/0255319 A1 | 11/2007 | Greenberg et al. |
| 2007/0291522 A1 | 12/2007 | Toba et al. |
| 2008/0208287 A1 | 8/2008 | Palermo et al. |
| 2008/0208300 A1 | 8/2008 | Pasch et al. |
| 2009/0149797 A1 | 6/2009 | Dacey, Jr. et al. |
| 2009/0192567 A1 | 7/2009 | Armstrong et al. |
| 2009/0254148 A1 | 10/2009 | Borgens et al. |
| 2011/0021943 A1 | 1/2011 | Lacour et al. |
| 2011/0071590 A1 | 3/2011 | Mounaim et al. |
| 2011/0077660 A1 | 3/2011 | Janik et al. |
| 2011/0137381 A1 | 6/2011 | Lee et al. |
| 2011/0160798 A1 | 6/2011 | Ackermann et al. |
| 2011/0190849 A1 | 8/2011 | Faltys et al. |
| 2011/0192720 A1 | 8/2011 | Blauw et al. |
| 2011/0221438 A1 | 9/2011 | Goodwill et al. |
| 2012/0016226 A1 | 1/2012 | Gertner |
| 2012/0053510 A1 | 3/2012 | Peters et al. |
| 2013/0035745 A1 | 2/2013 | Ahmed et al. |
| 2013/0053922 A1 | 2/2013 | Ahmed et al. |
| 2013/0238048 A1 | 9/2013 | Almendiger et al. |
| 2013/0274842 A1 | 10/2013 | Guant et al. |
| 2014/0031905 A1 | 1/2014 | Irazoqui et al. |
| 2014/0119480 A1 | 5/2014 | Keegan |
| 2014/0128865 A1 | 5/2014 | Gross |
| 2014/0135858 A1* | 5/2014 | Ahmed ............. A61N 1/36096 607/3 |
| 2014/0324129 A1 | 10/2014 | Franke et al. |
| 2015/0045675 A1 | 2/2015 | Chernomorsky |
| 2015/0073406 A1 | 3/2015 | Molsberger |
| 2015/0165210 A1 | 6/2015 | Kilgore et al. |
| 2015/0174397 A1 | 6/2015 | Bhadra et al. |
| 2015/0182742 A1 | 7/2015 | Ackermann et al. |
| 2015/0238764 A1 | 8/2015 | Franke |
| 2015/0293192 A1 | 10/2015 | Schmidt et al. |
| 2015/0316499 A1 | 11/2015 | Jacks et al. |
| 2016/0101286 A1 | 4/2016 | Bhadra et al. |
| 2016/0158542 A1 | 6/2016 | Ahmed |
| 2016/0235969 A1 | 8/2016 | Kilgore et al. |
| 2016/0235990 A1 | 8/2016 | Mashiach |
| 2016/0243353 A1 | 8/2016 | Ahmed |
| 2016/0256689 A1 | 9/2016 | Vallejo et al. |
| 2016/0263381 A1 | 9/2016 | Ahmed et al. |
| 2016/0271392 A1 | 9/2016 | Vallejo et al. |
| 2016/0271413 A1 | 9/2016 | Vallejo et al. |
| 2016/0331326 A1 | 11/2016 | Xiang et al. |
| 2016/0346533 A1 | 12/2016 | Bhadra et al. |
| 2017/0028192 A1 | 2/2017 | Ahmed et al. |
| 2017/0050024 A1 | 2/2017 | Bhadra et al. |
| 2017/0080244 A1 | 3/2017 | Chiel et al. |
| 2017/0100591 A1 | 4/2017 | Nudo et al. |
| 2017/0136235 A1 | 5/2017 | Molsberger |
| 2017/0136243 A1 | 5/2017 | Lee et al. |
| 2017/0312505 A1 | 11/2017 | Ahmed |
| 2018/0028824 A1 | 1/2018 | Pivonka et al. |
| 2018/0256886 A1 | 9/2018 | Bhadra et al. |

(56) References Cited

U.S. PATENT DOCUMENTS

| | | |
|---|---|---|
| 2018/0361155 A1 | 12/2018 | Bhadra et al. |
| 2019/0060640 A1 | 2/2019 | Bhadra et al. |
| 2019/0167996 A1 | 6/2019 | Bhadra et al. |
| 2019/0184160 A1 | 6/2019 | Franke et al. |
| 2019/0184173 A1 | 6/2019 | Franke |
| 2019/0269921 A1 | 9/2019 | Bhadra et al. |
| 2020/0001073 A1 | 1/2020 | Bhadra et al. |
| 2020/0129767 A1 | 4/2020 | Yoshida et al. |
| 2021/0038101 A1 | 2/2021 | Wu et al. |
| 2022/0088374 A1 | 3/2022 | Ackermann et al. |
| 2022/0096827 A1 | 3/2022 | Ackermann et al. |

FOREIGN PATENT DOCUMENTS

| | | |
|---|---|---|
| EP | 2 942 023 | 11/2015 |
| WO | WO 1998/15317 | 4/1998 |
| WO | WO 2007/082382 | 7/2007 |
| WO | WO 2008/048321 | 4/2008 |
| WO | WO 2008/140376 | 11/2008 |
| WO | WO 2010/042750 | 4/2010 |
| WO | WO 2013/188753 | 12/2013 |
| WO | WO 2015/142838 | 9/2015 |
| WO | WO 2017/044542 | 3/2017 |
| WO | WO 2017/062272 | 4/2017 |
| WO | WO 2017/106519 | 6/2017 |
| WO | WO 2018/085611 | 5/2018 |
| WO | WO 2018/187237 | 10/2018 |
| WO | WO 2019/157285 | 8/2019 |
| WO | WO 2019/164952 | 8/2019 |
| WO | WO 2020/010020 | 1/2020 |
| WO | WO 2021/102447 | 5/2021 |
| WO | WO 2021/102448 | 5/2021 |

OTHER PUBLICATIONS

International Search Report and Written Opinion in PCT Application No. PCT/US2020/062068 mailed Apr. 8, 2021 in 20 pages.
Ackermann, Jr, D. Michael, et al. "Separated interface nerve electrode prevents direct current induced nerve damage." Journal of neuroscience methods 201.1 (2011): 173-176.
Bhadra, Niloy, and Kevin L. Kilgore. "Direct current electrical conduction block of peripheral nerve." IEEE Transactions on Neural Systems and Rehabilitation Engineering 12.3 (2004): 313-324.
Borsook, David. "A future without chronic pain: neuroscience and clinical research." Cerebrum: the Dana forum on brain science. vol. 2012. Dana Foundation, 2012.
Brummer, S.B. et al. "Electrical Stimulation of the Nervous System: The Principle of Safe Charge Injection with Noble Metal Electrodes." Bioelectrochemistry and Bioenergetics 2: (1975) 13-25.
Bussel, Catelijne M., Dirk L. Stronks, and Frank JPM Huygen. "Successful treatment of intractable complex regional pain syndrome type I of the knee with dorsal root ganglion stimulation: a case report." Neuromodulation: Technology at the Neural Interface 18.1 (2015): 58-61.
Cogan, S.F., et al. "In Vitro Comparison of the Charge-Injection Limits of Activated Iridium Oxide (AIROF) and Platinum-Iridium Microelectrodes", IEEE Transactions on Biomedical Engineering, 52.9 (2005): 1612-1614.
Cogan, S.F., et al. "Potential-Biased, Asymmetric Waveforms for Charge-Injection With Activated Iridium Oxide (AIROF) Neural Stimulation Electrodes." 2006: 53(2): 327-332.
Donaldson et al. "When are actively balanced biphasic ('Lilly') stimulating pulses necessary in a neurological prosthesis?" Medical & Biological Engineering & Computing Jan. 1986: 24: 41-49.
ElBasiouny, S., et al. Modulation of motoneuronal firing behavior after spinal cord injury using intraspinal microstimulation current pulses: a modeling study. J. Appl. Physiol. 103 (2007) 276-286.
Fridman, Gene Y., and Charles C. Della Santina. "Safe direct current stimulation to expand capabilities of neural prostheses." IEEE Transactions on Neural Systems and Rehabilitation Engineering 21.2 (2013): 319-328.
Fridman, Gene Y., and Charles C. Della Santina. "Safe direct current stimulator 2: concept and design." In Engineering in Medicine and Biology Society (EMBC), 2013 35th Annual International Conference of the IEEE, pp. 3126-3129. IEEE, 2013.
Gabrielsson, Erik O., et al. "A four diode full wave ionic current rectifier based on bipolar membranes: Overcoming the limit of electrode capacity." Advanced Materials 26.30 (2014): 5143-5147.
Hasegawa, G., et al. "Impact of Electrolyte on Pseudocapacitance and Stability of Porous Titanium Nitride (TiN) Monolithic Electrode", Journal of The Electrochemical Society, 162.1 (2015): A77-A85.
Hollingworth, Milo, et al. "Single Electrode Deep Brain Stimulation with Dual Targeting at Dual Frequency for the Treatment of Chronic Pain: A Case Series and Review of the Literature." Brain sciences 7.1 (2017): 1-11.
Holtzheimer, Paul E., and Helen S. Mayberg. "Deep brain stimulation for psychiatric disorders." Annual review of neuroscience 34 (2011): 289-307.
Huang, C. et al. "Electrical stimulation of the auditory nerve: direct current measurement in vivo." IEEE Transactions on Biomed. Eng. vol. 46 No. Apr. 4, 1999 at 461-470.
Hurlbert, R. John. "Dose-response study of the pathologic effects of chronically applied direct current stimulation on the normal rat spinal cord." J. Neurosurg. 79 (Dec. 1993) 905-916.
Keifer, Orion Paul, Jonathan P. Riley, and Nicholas M. Boulis. "Deep brain stimulation for chronic pain: intracranial targets, clinical outcomes, and trial design considerations." Neurosurgery Clinics 25.4 (2014): 671-692.
Krum, Henry, et al. "Catheter-based renal sympathetic denervation for resistant hypertension: a multicentre safety and proof-of-principle cohort study." The Lancet 373.9671 (2009): 1275-1281.
Kim et al. "Electrochemical studies on the alternating current corrosion of mild steel under cathodic protection condition in marine environments", Electrochimica Acta 51, 2006, p. 5259-5267.
Kumsa, D. et al. Electrical neurostimulation with imbalanced waveform mitigates dissolution of platinum Electrodes. J. Neural Eng. 13 (2016): 1-5.
Kumsa, D et al. Electrical neurostimulation with imbalanced waveform mitigates dissolution of platinum electrodes. Neural Eng. (2018) 13(5): 1-8.
Kumsa, D.W., et al. "Electron transfer processes occurring on platinum neural stimulating electrodes: pulsing experiments for cathodic-first, charge-imbalanced, biphasic pulses for $0.566 \leq k \leq 2.3$ in rat subcutaneous tissues", Journal of Neural Engineering, 16 (2019): 1-11.
McHardy, J., et al., "An Approach to Corrosion Control during Electrical Stimulation", Annals of Biomedical Engineering, 5 (1977): 144-149.
Mendell, Lorne M. "Constructing and deconstructing the gate theory of pain." PAIN® 155.2 (2014): 210-216.
Merrill, Daniel R., Marom Bikson, and John GR Jefferys. "Electrical stimulation of excitable tissue: design of efficacious and safe protocols." Journal of neuroscience methods 141.2 (2005): 171-198.
Mortimer, J.T., et al., "Intramuscular Electrical Stimulation: Tissue Damage", Annals of Biomedical Engineering, 8 (1980): 235-244.
Nahin, Richard L. "Estimates of pain prevalence and severity in adults: United States, 2012." The Journal of Pain 16.8 (2015): 769-780.
Nakajima, H., et al. "Cervical angina: a seemingly still neglected symptom of cervical spine disorder?" Spinal cord 44.8 (2006): 509-513.
Neupane, M et al. Study of Anodic Oxide Films of Titanium Fabricated by Voltammetric Technique in Phosphate Buffer Media. Int. J. Electrochem. Sci., 4 (2009) 197-207.
Nielsen et al., "AC-Corrosion and Electrical Equivalent Diagrams", in: Proceedings of 5th International Congress, CeoCo, bruxelles, Belgium, 2000.
Schaldach, M, Fractal Coated Leads: Advanced Surface Technology of Genuine Sensing and Pacing, Progress in Biomedical Research, (2000): 259-272.

(56) References Cited

OTHER PUBLICATIONS

Scheiner, A., et al., "Imbalanced Biphasic Electrical Stimulation: Muscle Tissue Damage", Annals of Biomedical Engineering, 18 (1990): 407-425.
Specht, H. et al., Electrochemical properties and stability of PVD coatings for the application in cardiac and neurological stimulation, (2006).
Tjepkema Cloostermans, Marleen C., et al. "Effect of burst stimulation evaluated in patients familiar with spinal cord stimulation." Neuromodulation: Technology at the Neural Interface 19.5 (2016): 492-497.
Yang, Fei, et al. "Differential expression of voltage-gated sodium channels in afferent neurons renders selective neural block by ionic direct current." Science advances 4.4 (2018): eaaq1438 in 10 pages.

\* cited by examiner

|  | Trad - Conventional SCS | Trad - Burst SCS | Trad - HF - SCS | Example Waveform (non-limiting example values) |
|---|---|---|---|---|
| Typical Pulse width | 200-600uS | 1000uS | 30uS | ~500,000 – 10,000,000uS |
| Typical Pulse Frequency | 40-100Hz | 40 - 60Hz (500Hz intraburst) | 10,000Hz | ~.05 - 1 Hz |
| Typical Amplitude | 3.6-8.5mA | 0.5-2.7mA | 0.5-5mA | ~0.5-2mA |
| Typical Charge per pulse | 0.72-5.1uC (but only on about ~2-6% of time) | 0.5-2.7uC (only on ~20-30% of time) | 0.015-0.15uC | 250-20,000uC |

FIG. 8C

CURRENT BIAS AS A CONTROL MECHANISM FOR ELECTRODE OPERATION

INCORPORATION BY REFERENCE TO ANY PRIORITY APPLICATIONS

This application is a U.S. National Phase of International Application No. PCT/US2020/062068, filed Nov. 24, 2020, which claims the benefit of priority of U.S. Prov. Application No. 62/939,659, filed on Nov. 24, 2019, which are hereby incorporated by reference in their entireties. Any and all applications for which a foreign or domestic priority claim is identified in the Application Data Sheet as filed with the present application are hereby incorporated by reference under 37 CFR § 1.57.

BACKGROUND

This application relates, in some embodiments, to facilitating block, modulation or attenuation of biological signals through nerve tissue, including the processing of biological tissue in nervous system tissue, cardiac tissue, or other voltage-sensitive tissue.

The gate control theory of pain was developed in the 1960s and led to the advent of stimulation-based pain management therapies to reduce pain inputs from reaching the brain by selectively stimulating non-nociceptive fibers (non-pain transmitting fibers) in the spinal cord to inhibit transmission of pain stimuli to the brain (See Mendell, Constructing and Deconstructing the Gate Theory of Pain, Pain, 2014 February 155(2): 210-216). Current stimulation systems for spinal cord stimulation (SCS), which act on this gate control theory to indirectly reduce pain, typically have relied on stimulation signals in the <100 Hz frequency range, and recently in the kHz frequency range. Stimulation of the dorsal root ganglia, DRG, in a similar frequency range has also been employed to reduce segmental pain through the same mechanism.

However, technologies based on this premise have drawbacks as pain transmission inhibition is not complete and side effects such as paresthesia can be uncomfortable for patients. Therefore, it is desirable to have systems and methods of treating pain which more effectively block or attenuate pain signal transmission through pain fibers, or decrease the excitability of neurons which process pain signals, rather than indirectly reducing pain signals through gate-theory activation of non-nociceptive fibers, as well as avoid undesirable side effects. Furthermore, block or attenuation of neural tissue or neural activity has been implicated in not only affecting pain but also in the management of movement disorders, psychiatric disorders, cardiovascular health, as well as management of disease states such as diabetes.

SUMMARY

In some embodiments, disclosed herein are systems for electrically modulating tissue. The systems can include, for example, any number of: a current generator; at least one implantable working electrode, the at least one implantable working electrode configured to be in electrical communication with the current generator; at least one indifferent electrode; and a controller configured to signal the current generator to: generate a set of currents with a set of initial polarities to be delivered to the working electrodes, and the at least one indifferent electrode absorbs a bias current which is equal in magnitude and opposite in polarity to a summation of the set of currents.

In some configurations, the set of currents is sufficient to modulate electrically excitable tissue.

In some configurations, the at least one implantable working electrode comprises a high charge capacity material.

In some configurations, the bias current operates in an anodic polarity.

In some configurations, the bias current operates in a cathodic polarity.

In some configurations, the set of currents are configured to generate the bias current that biases the working electrode voltages cathodically.

In some configurations, the set of currents is configured to generate the bias current that biases the working electrode voltages anodically.

In some configurations, the set of currents are configured to generate the bias current that biases the indifferent electrode voltages cathodically.

In some configurations, the set of currents is configured to generate the bias current that biases the indifferent electrode voltages anodically.

In some configurations, the system also includes at least two working electrodes.

In some configurations, the initial polarity of at least one working electrode is cathodic.

In some configurations, the initial polarity of at least one working electrode is anodic.

In some configurations, the indifferent electrode is a skin surface electrode.

In some configurations, the indifferent electrode is a transcutaneous electrode or an implanted electrode.

In some configurations, the indifferent electrode comprises titanium.

In some configurations, the indifferent electrode has a working surface area of at least about 10 cm$^2$.

In some configurations, the indifferent electrode has a working surface area of at least about 100 cm$^2$.

In some configurations, the system is configured to generate a block of the excitable tissue.

In some configurations, the high charge capacity material comprises titanium nitride, tantalum, MP35N, and/or a combination thereof.

In some configurations, the high charge capacity material comprises tantalum coated with titanium nitride.

In some configurations, the system does not include any blocking capacitors (also may be referred to as coupling capacitors).

In some configurations, the bias current is fixed.

In some configurations, the bias current is variable.

In some configurations, the controller is configured to adjust the set of working electrode currents to modulate the bias current based on receiving data relating to one or any combination of capacitance, maximum current, and voltage.

In some configurations, the bias current is between about −10 μA and about −1 mA.

In some configurations, the bias current is between about −10 μA and about −100 μA.

In some configurations, the bias current is about −42 μA.

In some configurations, the bias current is evenly or unevenly split between a plurality of the implantable working electrodes.

In some configurations, the system is configured to inhibit water electrolysis in the patient.

In some configurations, the system is configured to inhibit corrosion of the working electrode.

In some configurations, the current generator is configured to generate DC current.

In some configurations, the current generator is configured to generate high frequency AC current.

In some configurations, the working electrode is configured to deliver at least about 500, 1,000, 2,000, 3,000, 4,000, 5,000, 10,000, 20,000 µC of charge, or more or less into excitable tissue without damaging the excitable tissue, or ranges including any two of the foregoing values.

In some configurations, the system is devoid of any mechanically moving parts.

Also disclosed herein are methods for electrically modulating tissue, comprising any number of: generating a set of currents with a set of initial polarities via a current generator; delivering the set of currents to at least one implanted working electrode; and absorbing a bias current through at least one indifferent electrode, wherein the bias current is equal in magnitude and opposite in polarity to a summation of the set of currents.

In some configurations, the set of currents is sufficient to modulate electrically excitable tissue.

In some configurations, the at least one implanted working electrode comprises a high charge capacity material.

In some configurations, the bias current operates in a cathodic polarity.

In some configurations, the set of currents generates the bias current that biases the working electrode voltages cathodically.

In some configurations, the set of currents generates the bias current that biases the working electrode voltages anodically.

In some configurations, the set of currents generates the bias current that biases the indifferent electrode voltages cathodically.

In some configurations, the set of currents generates the bias current that biases the indifferent electrode voltages anodically.

In some configurations, the method utilizes at least two working electrodes.

In some configurations, the initial polarity of at least one working electrode is cathodic.

In some configurations, the initial polarity of at least one working electrode is anodic.

In some configurations, the indifferent electrode is a skin surface electrode.

In some configurations, the indifferent electrode is a transcutaneous electrode or an implanted electrode.

In some configurations, the indifferent electrode includes titanium.

In some configurations, the indifferent electrode has a working surface area of at least about 10 cm2.

In some configurations, the indifferent electrode has a working surface area of at least about 100 cm2.

In some configurations, the method further comprises generating a block of the excitable tissue.

In some configurations, at least one working electrode comprises titanium nitride, tantalum, MP35N, and combinations thereof.

In some configurations, the bias current is fixed.

In some configurations, the bias current is adjustable based on receiving data relating to capacitance, maximum current, and voltage.

In some configurations, the bias current is between about −10 µA and about −1 mA.

In some configurations, the bias current is between about −10 µA and about −100 µA.

In some configurations, the bias current is about −42 µA.

In some configurations, the bias current is evenly or unevenly split between a plurality of the implantable working electrodes.

In some configurations, the method further comprises inhibiting water electrolysis in the patient.

In some configurations, the method further comprises inhibiting corrosion of the working electrodes.

In some configurations, generating DC current can include generating ultra low frequency currents.

In some configurations, the ultra low frequency currents can be less than about 1 Hz.

In some configurations, the ultra low frequency currents can be less than about 0.1 Hz.

In some configurations, the ultra low frequency currents can be less than about 0.01 Hz.

In some configurations, the method further comprises generating DC current, conventional frequency AC current, and/or high frequency AC current.

In some embodiments, disclosed herein are methods for electrically modulating tissue of a patient, comprising any number of: providing a system comprising a current generator; at least one implantable working electrode, the at least one implantable working electrode configured to be in electrical communication with the current generator; and at least one indifferent electrode; and/or measuring in-situ electrode capacity for setting a working electrode maximum charge, for monitoring one or more of: a condition of the electrode and/or an electro-physiological interface; for determining physiological attributes; and/or for interactively guiding electrode insertion and placement.

In some configurations, the method further comprises driving a current between a pair of the working electrodes, or any working electrode and the indifferent electrode.

In some configurations, the method further comprises measuring voltage between any two of the electrodes, such as between a working electrode and an indifferent electrode, between two working electrodes, between a working electrode and a reference electrode, or between an indifferent electrode and a reference electrode, for example.

In some configurations, each electrode is one of a working electrode, indifferent electrode, and reference electrode and each electrode could serve as one, or more than one of the aforementioned functions (e.g., a system or method could include one or more discrete working, indifferent, and reference electrodes). In some configurations, one or more of the electrodes could serve multiple functions (e.g. one electrode could be both a working and a reference electrode, a working and an indifferent electrode, and/or an indifferent and a reference electrode in different states).

In some configurations, the reference electrode comprises any unused working electrode. Any number of, or all of the electrodes can be switched between states, e.g., a reference electrode can be transformed into a working electrode, and a working electrode can be transformed into a reference electrode based on the phase of the stimulation pulse.

In some configurations, the method further comprises taking a measurement at a single point in time or continuously to a real-time response to a current waveform.

In some configurations, the method further comprises decomposing the waveform to derive the impedance (Ra, Cdl, Rf).

In some configurations, the method further comprises measuring a voltage drop along a physiological structure to evaluate the anatomy of said structure.

In some configurations, the method further comprises adjusting the electrode charge periodically or continuously to maximize electrode life.

In some configurations, the method further comprises ramping current amplitudes in conjunction with modulating bias current so that anodic/cathodic potentials are minimized so the electrode gradually shifts into the desired voltage range.

In some configurations, disclosed herein are methods for reducing power of an electrical tissue modulation system, comprising any number of: delivering electrical stimulation to tissue of a patient; duty cycling the stimulation such that the effect of stimulation persists for a preset period of time, and once the therapeutic effect has occurred, suspending the stimulation for an empirically determined period and then cycled on before the therapeutic effect diminishes. In some embodiments, the duty cycle (on time) can be, for example, about, at least about, or no more than about 5%, 10%, 15%, 20%, 25%, 30%, 35%, 40%, 45%, 50%, 55%, 60%, 65%, 70%, 75%, 80%, 85%, 90%, 95%, or more or less, and ranges including any two of the foregoing values.

In some embodiments, the duty cycle can be 100% (or any of the foregoing values or ranges including any two of the foregoing values), while the amplitude can be set at a first level for a first period of time, and then changed (e.g., increased or decreased) to a second level for a second period of time.

The second level can be, for example, about, at least about, or no more than about 5%, 10%, 15%, 20%, 25%, 30%, 35%, 40%, 45%, 50%, 55%, 60%, 65%, 70%, 75%, 80%, 85%, 90%, 95%, or more or less relative to the first level, and ranges including any two of the foregoing values.

The second period of time can be, for example, at least about, about, or no more than about 25%, 50%, 75%, 100%, 125%, 150%, 175%, 200%, or more or less relative to the first period of time, and ranges including any two of the foregoing values.

In some embodiments, a device can deliver an electrical waveform at full amplitude for a period of time, then reduce amplitude to lower values. As one non-limiting example, the initial waveform amplitude is A and after time (e.g., after block is achieved) amplitude is held at A/2 or ¾ A or other levels as disclosed elsewhere herein to reduce power consumption as well as to use less of electrode capacity.

In some configurations, also disclosed herein are methods for delivering electrical stimulation to tissue of a patient such that the effect of stimulation persist for a preset period of time beyond the stimulation.

In some configurations, the therapeutic effect is pain reduction and/or others as disclosed elsewhere herein.

In some embodiments, disclosed herein are methods for reducing patient sensation by controlling the rise time and fall times of electrical currents. In some configurations, the rise times and fall times are limited from about 50 milliseconds to about 5 seconds, or more or less.

In some embodiments, disclosed herein are systems for electrically modulating tissue, comprising any number of: a current generator; at least one implantable working electrode, the at least one implantable working electrode configured to be in electrical communication with the current generator; at least one indifferent electrode; and a controller configured to signal the current generator to: generate a set of currents with a set of initial polarities to be delivered to the working electrodes. The at least one indifferent electrode can absorb a bias current which is equal in magnitude and opposite in polarity to a summation of the set of currents.

In some configurations, the set of currents comprise ultra low frequency currents, such as, for example, less than about 1 Hz, 0.1 Hz, 0.01 Hz, or less.

In some configurations, a method for delivering electrical stimulation to tissue of a patient, such that the effect of stimulation persist for a preset period of time beyond stimulation comprises any one or more of the embodiments described in the disclosure.

In some embodiments, a system for electrically modulating tissue, comprises any one or more of the embodiments described in the disclosure.

In some embodiments, a method for electrically modulating tissue, comprises any one or more of the embodiments described in the disclosure.

In some embodiments a current delivery system or method could include any number of features or combination of features as disclosed herein.

In some embodiments, electrical neuromodulation of tissue including delivery of high charge densities via an ultra low frequency waveform and use of at least one indifferent electrode to absorb a bias current can unexpectedly, advantageously, and safely enable continued suppression of neural activity after cessation of current delivery (wash-out period), which can provide multiple benefits. For example, power can be saved or, stated differently, power consumption can be slowed. In another example, the sudden return of neural activity can be prevented in case of device failure (e.g., connection, battery, etc.), which can improve safety and/or enable patient/physician intervention during prolonged suppression period. Similarly, the rapid return of pain in the event of device failure and/or the rapid return of sympathetic signaling that may lead to acute sympathetic events (such as acute decompensation or cardiac arrhythmias) can be prevented. In yet another example, when implemented as an electronic medicine dosing system/method, a long-lasting therapeutic benefit can be created from acute application. Furthermore, such systems and methods can be very safe, inhibiting/minimizing the creation of toxic species at the electrode-nerve interface.

BRIEF DESCRIPTION OF THE DRAWINGS

FIG. 8C illustrates a table of values related to various SCS waveforms.

DETAILED DESCRIPTION

Figure 1A:
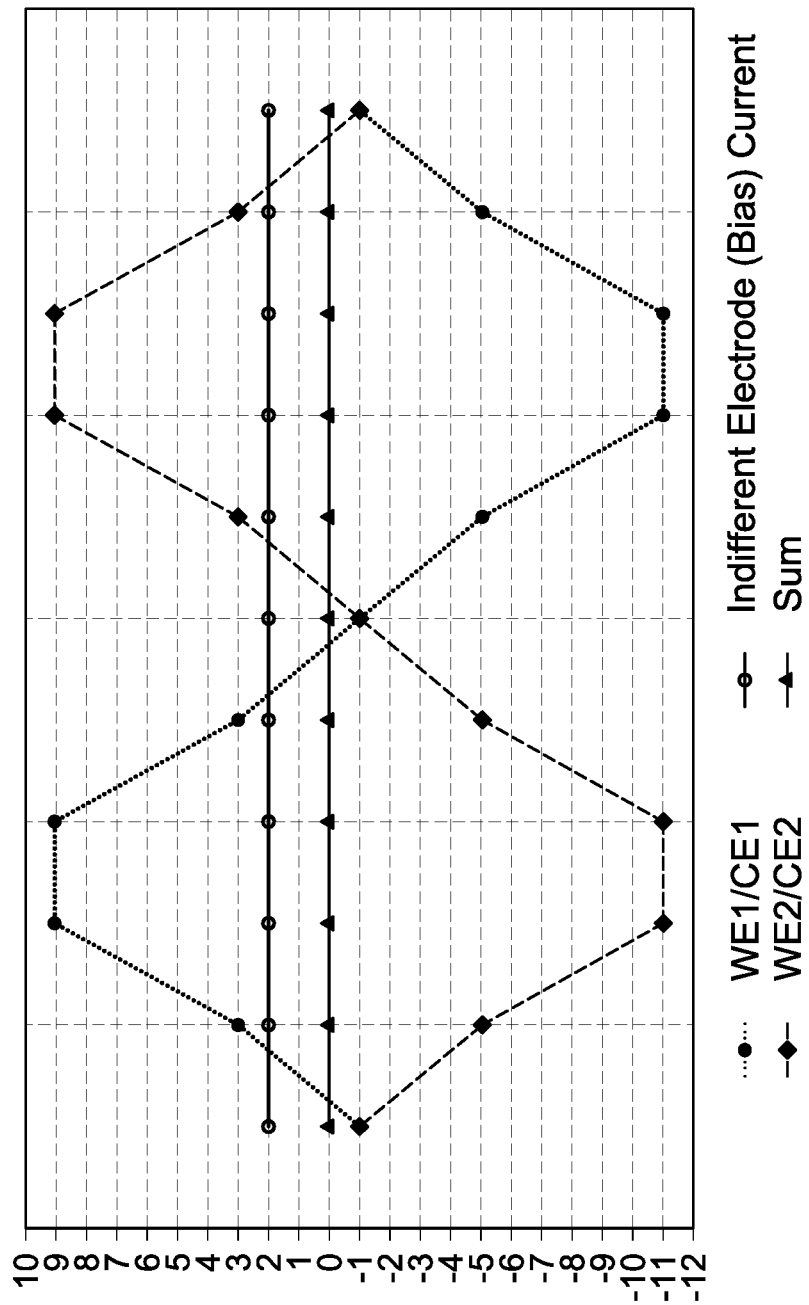
FIG. 1A schematically illustrates an embodiment of a waveform between working electrodes with a constant bias current.

This application describes, in some aspects, methods and systems for management of chronic and acute pain states via application of direct current (DC) to facilitate nerve block or attenuation including nerve hypersuppression, or nerve block without rapid reversibility or recovery after direct current application has been removed or stopped. What is disclosed in some embodiments are systems and electrodes for delivering blocking or attenuating direct current (DC) to neural tissue by delivering cycled cathodic and anodic current. In some embodiments these systems involve high-charge capacity materials. Tissue safety can be maintained by operating the electrode below reaction potentials for undesired reactions as well as by limiting the amount of irreversible reactions, such as electrolysis of water, or oxidation and reduction of water ($H_2O$), which create harmful reactive species such as OH—, H+ or oxygen free radicals, and in some cases by maintaining a bias current, as discussed further herein. More generally, neuromodulation as described within refers to modulation of activity, excitability or cellular state of neural tissue (including but not limited to neurons and/or glial cells), cardiac tissue or other neural or non-neural excitable tissue or tissue which can be impacted by electrical fields or currents. In some embodiments, either the anodic or cathodic phases of a delivered waveform to a patient, or both the anodic and cathodic phases can have a therapeutic effect on electrically excitable tissue, such as neural tissue for example.

Not to be limited by theory, the propagation of action potentials in electrically excitable tissue, e.g. neural tissue, leads to refractory periods on the order of milliseconds for sodium channels, typically between about 1 ms and about 20 ms, or between about 2 ms and about 5 ms for the combined absolute and relative refractory periods, thus very (e.g., ultra low frequency) AC current waveforms with half periods meaningfully greater than this refractory period (e.g., greater than about 1 ms, 1.5 ms, 2 ms, 2.5 ms, 3 ms, 10 ms, 30 ms, 50 ms, 100 ms, 300 ms, 500 ms, 1000 ms, 2000 ms, 5000 ms, 6000 ms or more) and have sufficiently low differential rates (e.g. rise and fall-times) to not induce action potentials can also be used to create tissue blockade or attenuation, and will be perceived by electrically excitable tissue as a direct current stimulus. As such, direct current (DC) as defined herein is inclusive of ultra low frequency AC current waveforms that are perceived as and functionally is direct current from the perspective of the tissue whose action potentials or neural processing are being modulated. The ultra low frequency could be, for example, less than about 10 Hz, 9 Hz, 8 Hz, 7 Hz, 6 Hz, 5 Hz, 4 Hz, 3 Hz, 2 Hz, 1 Hz, 0.5 Hz, 0.1 Hz, 0.05 Hz, 0.01 Hz, 0.005 Hz, 0.0001 Hz, or ranges including any two of the foregoing values so long as the direction of current flow is constant over at least the entire refractory period of the target tissue, or at least twice as long, or at least five times as long, or at least ten times as long as the refractory-causing membrane channel time constant (for example, fast sodium channel inactivation gate time constant).

Chronic pain is a significant burden on individuals and society as a whole. Nearly 50 million adults are estimated to have significant chronic or severe pain in the US alone. (See Nahin, Estimates of Pain Prevalence and Severity in Adults: United States, 2012, The Journal of Pain, 2015 August 16(8): 769-780) Worldwide, chronic pain is estimated to affect more than 1.5 billion people. (Borsook, A Future Without Chronic Pain: Neuroscience and Clinical Research, Cerebrum, 2012 June) While surgical techniques are sometimes applied to remove a specific source of pain, frequently due to impingement of a nerve, in many cases the precise cause of pain is not clear and cannot be reliably addressed via a surgical procedure. Pain management can alternatively be addressed by overwhelming the central nervous system with stimulating signals that prevent registration of pain inputs (gate control theory of pain). Typically, this stimulation in the case of spinal cord stimulation (SCS) is performed using metal electrodes and alternating current (AC) stimulation to produce these additional stimulating signals to prevent pain sensation. However, one major drawback is the presence of paresthesia, a sensation of tingling in the innervated region downstream from the stimulated nerve. Methods to eliminate paresthesia which patients can find discomforting have led to different means of stimulation from conventional tonic SCS (~30-120 Hz) stimulation including high frequency stimulation (~10 kHz) and burst stimulation (e.g., five pulses at 500 Hz delivered 40 times per second). (Tjepkema-Cloostermans et al, Effect of Burst Evaluated in Patients Familiar With Spinal Cord Stimulation, Neuromodulation, 2016 July 19(5):492-497).

An alternative means to manage pain signaling to the central nervous system is to prevent conduction of the pain signals from the peripheral signal source by directly blocking or attenuating the pain signals as compared to masking the pain signals by generating alternative neural inputs to crowd out and inhibit pain signal transmission as in traditional SCS and gate theory. One means to do this is by applying a direct current (DC) to a nerve to prevent action potential (AP) generation and transmission. Because this does not stimulate the nerve as in traditional stimulation, paresthesia can be avoided. The mechanism leading to AP block has been attributed to a depolarization block or hyperpolarization block that deactivates the sodium channels required for an action potential event under the electrode site. (See Bhadra and Kilgore, Direct Current Electrical Conduction Block of Peripheral Nerve, IEEE Transactions on Neural Systems and Rehabilitation Engineering, 2004 September 12(3): 313-324). Wide dynamic range (WDR) neurons integrate pain signals and have also been implicated as a contributing source of pain in patients, and application of direct current (DC) is well positioned to reduce this activity and may impact associated inhibitory and excitatory neurons that drive WDR activity.

The unmitigated use of direct current has long been known to be dangerous to nerve tissue due to creation of toxic species at the electrode-nerve interface. As such, systems and methods that facilitate safe delivery of direct current therapy would be highly desirable. In some embodiments, systems and methods can be configured to treat nociceptive pain. In some embodiments, systems and methods of treating pain and other medical can involve selective blockade of antero-lateral column tissue in the spinal cord. Furthermore, some embodiments relate to systems and methods of treating pain by the aforementioned systems and methods, specifically through selective blockade of dorsal root tissue and/or dorsal root ganglia. Moreover, in some embodiments, disclosed herein are systems and methods of treating pain, specifically through blockade or attenuation of one or more peripheral nerves.

In some embodiments, systems and methods can safely block or attenuate pain signals (which includes modulation of pain processing) in the spinal column by delivering very low frequency stimulation in the epidural space for up to two weeks or more, to achieve clinically measurable pain reduction in patients with chronic low back pain who are candidates for spinal cord stimulation (SCS).

With targeted nerve block, pain from specific dermatomes and pain in regional body sites can be managed. A number of localized targets implicated in moderating pain signal transduction can be addressed. For example, both more centrally located nerve tissues such as the spinothalamic tract and dorsal root ganglion can be targeted to manage lower back pain, sciatica, and complex regional pain syndrome (CPRS) among other pain considerations.

In some embodiments, an electrode can include a contact comprising a high charge-capacity material. The electrode contact can have in some cases a geometric surface area of between about 1 $mm^2$ and about 10 $mm^2$, or about 1 $mm^2$, 2 $mm^2$, 3 $mm^2$, 4 $mm^2$, 5 $mm^2$, 6 $mm^2$, 7 $mm^2$, 8 $mm^2$, 9 $mm^2$, 10 $mm^2$, 20 $mm^2$, 50 $mm^2$, 100 $mm^2$, or ranges including any two of the foregoing values. The electrode contact itself can be fabricated of a high charge capacity material, such as those described, for example, in U.S. Pat. No. 10,071,241 to Bhadra et al., which is hereby incorporated by reference in its entirety. Alternatively, the electrode contact can comprise a base at least partially, or entirely coated with a high charge capacity material. In some embodiments, a high charge capacity material can have a Q value of at least about 25, 50, 100, 200, 300, 400, 500, 1,000, 2,500, 5,000, 10,000, 50,000, 100,000, 500,000, or more µC, or ranges including any two of the foregoing values. The Q value of an electrode contact can refer to the total amount of charge that can be delivered through an electrode contact before the electrode contact begins generating irreversible chemical reactions at a rate that cannot be cleared through the body's nominal transport mechanism. These chemical reactions include but are not limited to oxygen or hydrogen evolution, or dissolution of the electrode materials. Non-limiting examples of high charge capacity materials are platinum black, iridium oxide, titanium nitride, tantalum, silver chloride, poly(ethylenedioxythiophene) and suitable combinations thereof. The electrodes can comprise fractal coatings or high surface area formats in some embodiments. High charge capacity materials may be configured to be monolithic or as coatings on base substrates. Non-limiting examples of substrates for coating include stainless steel such as 304 and 316LVM, nickel-cobalt-chrome alloys such as MP35N®, platinum and platinum-iridium, titanium, nickel-titanium alloys such as Nitinol. In some embodiments, the electrodes can include tantalum coated with titanium nitride. Tantalum as one non-limiting example can be a particularly advantageous material for its superior radiopacity, thus allowing for improved implantation, verification, and/or removal of implantable neuromodulation devices. To generate more surface area for the electrochemical reactions to occur, the traditional electrodes may be made from high surface area to volume structures such as electroplated surfaces, (e.g., platinum black/electrodeposited iridium oxide for example), roughened surfaces, woven surfaces, patterned surfaces, reticulated foam structures, porous sintered bead structures, nano- or micro-patterned structures to expose additional material surface area. In some embodiments, the electrode can be a SINE (separated-interface nerve electrode) or EICCC (electron to ion current conversion cell) electrode in which an electrode is immersed in an electrolyte solution which is in contact with an ion-conductive material-electrolyte solution interface with an ion-conductive material that electrically contacts the cardiac tissue or area proximal to cardiac tissue, as described, for example, in U.S. Pat. No. 9,008,800 to Ackermann et al., and U.S. Pub. No. 2018/0280691 to Ackermann et al., which is hereby incorporated by reference in their entireties.

In some embodiments, disclosed herein are systems and methods for safely and efficaciously stimulating neural tissue that can advantageously utilize a variety of waveforms from DC to high frequencies. Stimulation with DC, although potentially very useful, has not been commercially utilized for neural modulation because neurostimulation systems capable of delivering DC safely for long periods of time have not been available. Available commercial systems prevent DC delivery to limit irreversible electrochemical reactions, relying on charge balancing mechanisms. These systems can include blocking the DC component with capacitors, blocking capacitors (coupling capacitors), or mechanisms that remove charge accumulation at the end of a stimulation cycle. While reliable, typical capacitors limit charge to less than about one millicoulomb (mC) per phase, disallowing the use of ultra-low frequency signals at large charge magnitudes in excess of this charge capacity. The other widely utilized technique relies on actively balanced current sources, but these require redundancy to be fault tolerant and typically do not deliberately control electrode voltages important for some electrode technologies and have not been shown to be advantageous for long-term high charge delivery. Active systems in conjunction with coatings have been utilized in such devices as retinal implants to increase charge densities to about ~2 $mC/cm^2$, but these densities are still insufficient to allow use of very high charge per phase waveforms required by DC or very low frequency waveforms with sufficient current amplitude.

Some embodiments involve high surface area electrode coatings in conjunction with a bias current such as, for example, a DC bias to maintain the electrode voltages in the optimal range for a particular electrode material for long term operational durability. This approach can boost the charge per phase from about 50 $\mu C/cm^2$ used in conventional systems to about or at least about 5,000 $\mu C/cm^2$, 25,000 $\mu C/cm^2$, 50,000 $\mu C/cm^2$, and beyond in some cases without, for example, causing damage to either the electrode or the electrically excitable tissue. Systems and methods configured to allow for an intentional net bias current, e.g., DC bias, such as via a control system, can, in some cases, advantageously maintain the health of the high charge capacity electrodes (by preventing or inhibiting corrosion, e.g., oxidation, or other damage to the electrodes) as well as minimizing or preventing undesired reactions and generation of species such as $OH^-$, $H^+$ or oxygen free radicals that can lead to tissue damage. Peroxide formation is another non-limiting example of an undesired reaction that can be prevented or inhibited with systems and methods as disclosed herein, as well as other undesired reactions depending on the material (e.g., metallic material or alloy, for example) and its location.

In some embodiments, the charge per anodic and/or cathodic phase is, for example, about 1,000 µC, 1,500 µC, 2,000 µC, 2,500 µC, 3,000 µC, 3,500 µC, 4,000 µC, 4,500 µC, 5,000 µC, 5,500 µC, 6,000 µC or more or less, such as between about 4,000 µC and about 5,000 µC per phase, and ranges including any two of the foregoing values.

In some embodiments, systems and methods for the delivery of current via implanted electrodes do not include capacitors such as blocking capacitors (coupling capacitors).

In some embodiments, systems and methods for the delivery of current via implanted electrodes do not include resistors.

In some embodiments, the bias current is the current resulting from the summation of the currents being simultaneously delivered to the electrode contacts or working electrodes in proximity to the target excitable or voltage-sensitive tissue. In some embodiments, the bias current is equal in magnitude and opposite in polarity to the summation of the currents being simultaneously delivered to the electrode contacts or working electrodes. In some embodiments, the currents being simultaneously delivered to the electrode contacts or working electrodes can be adjusted to modulate the bias current.

In some embodiments, the bias current can be a cathodic bias current (for example, for TiN or tantalum electrodes). In some embodiments, the bias current can be an anodic bias current, with (+) positive values substituted for any (−) values disclosed herein (for example, for IrOx electrodes). In some embodiments, the total bias current can be, for example, between about −10 µA and about −1 mA, between about −10 µA and about −100 µA, between about −0.01 µA and about −1000 µA, between about −0.01 µA and about −0.1 µA, between about −0.1 µA and about −1 µA, between about −1 µA and about −1000 µA, between about −20 µA and about −100 µA, or about −0.01 µA, −0.05 µA, −0.10 µA, −0.50 µA, −1 µA, −5 µA, −10 µA, −15 µA, −20 µA, −25 µA, −30 µA, −35 µA −40 µA, −45 µA −50 µA, −55 µA, −60 µA, −65 µA −70 µA, −75 µA −80 µA, −85 µA −90 µA, 95 µA −100 µA, or more or less, or ranges including any two of the foregoing values. The bias current can be, for example, values as disclosed herein, and in some embodiments between about −40 µA and about −50 µA, such as about −40 µA, −41 µA, −42 µA, −43 µA, −44 µA, −45 µA, −46 µA, −47 µA, −48 µA, −49 µA, −50 µA, and ranges including any two of the foregoing values. As noted, the bias current can be either negative as noted in some values and ranges herein, or alternatively positive (e.g., the absolute value) of any of the values or ranges of values disclosed herein, including but not limited to those in this paragraph. In some embodiments, the total bias current can be split, e.g., evenly among the number N of working electrodes. For example, in a bipolar system with 2 working electrodes, the bias current of each working electrode can be the total bias current/2, such as −42 µA/2=−21 µA or +42 µA/2=+21 µA in some embodiments, where the total bias current is the offset from the perspective of the indifferent electrode, and the bias current/N is from the perspective of the working electrode, wherein N is the number of working electrodes. The bias current may be even larger or smaller in amplitude, e.g. to accommodate use in embodiments with larger or smaller electrode surface areas.

In some embodiments, the bias current can be fixed. In some embodiments, the bias current can be variable, and be altered depending on voltage and/or other measurements (e.g., when a voltage waveform exhibits linearity or non-linearity, for example).

FIG. 1A schematically illustrates an embodiment of a waveform between working electrodes with a constant bias current. As illustrated, the example waveform is bipolar, and each biased down by 1 unit of current leading to a total bias current of 2 units, and all currents sum to zero. Other bias magnitudes can be as described, for example, elsewhere herein.

In some embodiments, the bias current resulting from the working electrode currents can be delivered to one, two, or more indifferent electrodes (e.g., only a single indifferent electrode in some embodiments). The indifferent electrode may be configured to be a passive current sink or source or alternatively may be an active current sink or source. In some embodiments, the indifferent electrode(s) can have a relatively high working surface area to minimize the current density on the electrode surface and minimize or prevent discomfort or other sensations of the delivered current to the patient. The indifferent electrode may be implanted, be a transcutaneous electrode, or be a body surface electrode. In some embodiments, the indifferent electrode can have a working surface area of about or at least about 1 $cm^2$, 5 $cm^2$, 10 $cm^2$, 25 $cm^2$, 50 $cm^2$, 75 $cm^2$, 100 $cm^2$, 125 $cm^2$, 150 $cm^2$, 175 $cm^2$, 200 $cm^2$, 500 $cm^2$, 1000 $cm^2$, or ranges including any two of the foregoing values.

A transcutaneous indifferent electrode can be skin adherent utilizing, for example, adhesives, and be configured to pass offset/bias current continuation for the wear duration without substantially increasing voltage. The transcutaneous indifferent electrode may comprise electrically conductive materials such as hydrogels and the like in combination with adhesives to promote skin adherence. The wear duration can be, for example, at least 3, 4, 5, 6, 7, 8, 9, 10, 11, 12, 13, 14, or more days, or ranges including any two of the foregoing values, such as between about 7-10 days in some cases.

In some embodiments, a transcutaneous indifferent electrode can have a relatively low DC resistance (without skin resistance), such as, for example, less than about 1,000, 900, 800, 700, 600, 500, 400, 300, 200, 100, 90, 80, 70, 60, 50, 40, 30, 20, 10 Ohms, or more or less, and ranges including any two of the foregoing values.

In some embodiments, the increase in driving voltage of the system from the initial driving voltage will be less than 100 mV, 200 mV, 300 mV, 400 mV, 500 mV, 600 mV, 700 mV, 800 mV, 900 mV, 1,000 mV, 1,100 mV, 1,200 mV, 1,300 mV, 1,400 mV, 1,500 mV or more over the wear duration.

In some embodiments, an implantable indifferent electrode can be the housing, e.g., can of an implantable pulse generator of a neuromodulation system and may comprise titanium e.g., grade 1, grade 2, or grade 4 titanium as non-limiting examples or platinum or platinum plated titanium.

Due to their exponential nature as a function of voltage, irreversible electro-chemical reactions cannot be completely avoided. These reactions need to be limited such that the byproducts can be removed by the transport properties of surrounding tissues including diffusion and fluid flow.

Reversible electro-chemical reactions need to be reversed and byproducts recovered to the extent possible such that their byproducts can be removed by the surrounding tissues without accumulating to remain below tissue toxicity levels. The rate of removal is dependent upon the location in the body and the mechanical and electromechanical characteristics of the electrode.

Charge can be categorized as recoverable and un-recoverable. One important goal in some cases is to minimize the un-recoverable charge to a level that the body can safely transport away generated byproducts resulting from reactions due to the un-recoverable charge to minimize tissue damage.

Electro-chemical reactions exponentially increase with voltage potential, therefore controlling voltages on electrode surfaces can be an effective way to minimize undesired electro-chemical reactions. These voltage potentials can be controlled by biasing the electrode with DC or similar current.

Electrodes designed to produce uniform current densities (or relatively uniform) allow the use of average voltage to be representative of the electro-chemical reactions.

Each type of electrode material has specific operating ranges (appropriate charge capacities and voltage ranges for predominantly reversible and limited irreversible reactions) and it can be highly advantageous to operate within those ranges in some embodiments. For example, cathodically biasing titanium nitride and/or tantalum electrodes mitigates formation of oxides that occur with anodic voltages. In another example, anodically biasing titanium develops a protective oxide on the titanium surface that can reduce material corrosion. Any conductive materials (e.g. metals, conductive coatings) exposed to surrounding fluid or electrolyte can be subject to corrosion, and biasing these materials can provide protection against deleterious corrosion to enhance the longevity of service of the active conductive elements of the system. These active conductive elements may comprise any exposed metal on an IPG, for example, that passes current or is subject to voltage potentials that drive undesirable reactions.

In traditional stimulation systems, AC currents are delivered through a series capacitor with no DC leakage to guarantee charge is balanced. However, electrochemical reactions are exponential, time dependent, and not fully symmetrical, so capacitors even at lower voltages do not guarantee elimination of irreversible reactions. Capacitors are an economical way to prevent imperfect (realizable) current sources and sinks from introducing DC and a reliable way of isolating faults caused by current sources and sinks. In some embodiments that can overcome these issues, systems and methods do not include any such capacitors also known as blocking capacitors.

In some embodiments, chronic electrode materials are biocompatible and do not easily dissolve.

In some embodiments, disclosed herein are systems and methods of stimulation with full spectrum stimulation.

Hybrid waveforms: conventional stimulation waveforms are intentionally AC and have an unintentional DC component. The unintentional DC component is conventionally kept as low as possible to balance the charge leaving the voltage equilibrium point not directly controlled. By intentionally injecting or absorbing non-AC current (referred to herein as a bias current), deliberate control of the voltage equilibrium point (quasi-steady state) and range can be achieved. Such deliberate control can be achieved, for example, via one or more of the following non-limiting examples: (a) in the case of monopolar bias current, e.g., DC Bias or similar current injection or absorption can occur by creating an imbalance on one or more WE (working electrodes) and one or more CE/IE (counter electrodes operating as the Indifferent Electrode) without current control that will absorb all of the current, (b) in the case of bipolar bias current, e.g., DC Bias or similar current injection or absorption can occur by creating an imbalance on one or more WE (working electrodes) and one or more CE (counter electrodes) where the excess current will be absorbed on the Indifferent Electrode, (c) and in the case of multipolar some hybrid of (a) and (b). This can create an imbalance on each WE and CE/IE. Bias current or similar current injection or absorption can occur by creating an imbalance between N number of CEs and M number of WEs and absorbing the difference with at least one indifferent electrode which may or may not be the same as the CE (e.g. source and sink are imbalanced on multiple current outputs); during bipolar operation between two contacts, the WE and CE change between the two contacts depending on the system polarity and the indifferent electrode or electrodes (IE) represents a third electrode type which absorbs the imbalance between the WE and CE regardless of polarity. In some embodiments, a system or method can include only a single WE and a plurality of CEs to advantageously reduce the stress and driving voltages on electrodes. In some embodiments two WEs can be operated together for a given collective current output to reduce the driving voltages of the two WEs as compared to having the same current output on a single WE.

DC or similar charge injection: Deliberate control of the voltage equilibrium can be utilized for the purpose of adjusting electrode potentials (quasi-steady state voltage), and can be achieved using, for example, a generalized PID control algorithm where the process variable (PV) can be some environmental measure including but not limited to: a maximum peak voltage; a minimum peak voltage; a combination of a specified voltage rail and peak-to-peak voltage; average voltage levels; root-mean-square; running average; absolute voltage change; rate of voltage change; access resistance; electrical property of the electrode (e.g. capacitance); charge (accumulation of current over time); and/or chemical measurement, such as pH.

A bias current, e.g., DC or similar charge injection waveform can be derived as a function of electrode material, frequency composition of waveform, pH, local perfusion, tissue type, the type of tissue, target for stimulation, and/or the distance from target tissue. The waveform can be, for example, any one or more of the following: a constant value; a time-varying value; dynamically adjusted to achieve voltage operating points above based upon an algorithm that may be based on one or more of the following parameters: cathodic current amplitude to anodic current amplitude; duty cycle or ratio of cathodic phase time to anodic phase time; interphase or interperiod interval; overall charge in cathodic or anodic phases; and/or types of waveforms in the cathodic or anodic phase. These items assume a current stimulation source but can also be applicable for a voltage stimulator where voltages are used in place of currents to determine the parameters above.

In some embodiments, multidimensional field shaping can be implemented. In some embodiments, multiple electrodes can be spatially employed to focus energy in targeted localities including the dorsal root entry zone; spinal column; spinothalamic tract; and/or any specific spatial region in and around the stimulating electrodes. In some embodiments, systems and methods can include temporally using frequency and phase shift to vary the field such that the focal point moves with time; and/or recruits different classes and diameters of neurons, axons, or ion channels.

In some embodiments, systems and methods can be configured for voltage and/or pulse clamping. Pulse clamping can provide a method of forcing a voltage on the electrode surface to avoid irreversible chemical reactions. Pulse clamping can include control of the voltage, such as, for example, during an interpulse interval, to control the electrochemistry of the electrode so as to "reset" the electrode or control the electrochemistry to allow for more charge to be injected in the next stimulation cycle.

Clamping can also be utilized to increase charge injection capabilities. Clamping and/or utilizing current limits can limit the recruitment of neural tissue and voltage slew rate on an electrode surface. Current passing through the electrode can be used to assess the current state of the electrode, allowing adaptive control of the stimulus waveform to affect parameters including those mentioned otherwise herein.

In some embodiments, systems and methods can generate waveform shapes, such as defined by B-splines, infinitely differentiable functions, and/or other mathematical functions to control/limit the rate of voltage and current change to: limit/control the onset of neural recruitment or the opposite; and/or limit or control the electrochemical reactions or the opposite. Asymmetric waveforms can be generated where the duration and amplitude of the cathodic phase is different from the duration and amplitude of the anodic phase. The shape of the waveform may comprise changes in amplitudes over time including a linear and non-linear, monotonic or non-monotonic, increases and decreases in amplitude as well as periods of constant amplitude or zero amplitude. In one preferential embodiment a waveform may comprise a sequence with a current with increasing amplitude, a substantially constant current amplitude, a current with a decreasing amplitude followed by the same sequence of the opposite polarity. The magnitude of the slope of the increasing current amplitude may be greater than, equal to, or lower than the magnitude of the slope of the decreasing current. To mitigate undesired neural activity, the magnitude of the slope of the increasing current amplitude may be configured to be lower than the magnitude of the slope of the decreasing current. Furthermore, the transition regions between increasing, substantially constant, and decreasing current amplitudes may be smoothed and rounded to control/limit the rate of voltage and current change to limit/control the onset of neural recruitment.

In some embodiments, an amplitude waveform can have various rise time/durations, plateau time/durations, and/or fall time/duration depending on the desired clinical result.

In some embodiments, a waveform can include a rise time of about, at least about, or no more than about 0.5 s, 1.0 s, 1.5 s, 2.0 s, 2.5 s, 3.0 s, 3.5 s, 4.0 s, 4.5 s, 5.0 s, 6 s, 7 s, 8 s, 9 s, 10 s, 15 s, 20 s, or more or less, or ranges including any two of the foregoing values. The rise time could be a single continuous rise, or multiple rises interspersed with one or more plateau and/or falls in some embodiments.

In some embodiments, a waveform can include a plateau time of about, at least about, or no more than about 0.5 s, 1.0 s, 1.5 s, 2.0 s, 2.5 s, 3.0 s, 3.5 s, 4.0 s, 4.5 s, 5.0 s, 6 s, 7 s, 8 s, 9 s, 10 s, 15 s, 20 s, or more or less, or ranges including any two of the foregoing values. The plateau time could be a single continuous plateau, or multiple plateaus interspersed with one or more rises and/or falls in some embodiments.

In some embodiments, a waveform can include a fall time of about, at least about, or no more than about 0.5 s, 1.0 s, 1.5 s, 2.0 s, 2.5 s, 3.0 s, 3.5 s, 4.0 s, 4.5 s, 5.0 s, 6 s, 7 s, 8 s, 9 s, 10 s, 15 s, 20 s, or more or less, or ranges including any two of the foregoing values. The fall time could be a single continuous fall, or multiple falls interspersed with one or more plateaus and/or rises in some embodiments.

In some embodiments, the waveform starts cathodic first and falls, plateaus, then rises then the waveform becomes anodic and rises, plateaus, and then falls for a set time period. In some embodiments, the waveform starts anodic first. The set time period can be, for example, about, at least about, or no more than about 1 s, 2 s, 3 s, 4 s, 5 s, 6 s, 7 s, 8 s, 9 s, 10 s, 11 s, 12 s, 13 s, 14 s, 15 s, 16 s, 17 s, 18 s, 19 s, 20 s, 25 s, 30 s, 35 s, 40 s, 45 s, 50 s, 55 s, 60 s, or more or less, or ranges including any two of the foregoing values. In some embodiments, the cathodic and anodic phases are separated by a third plateau type.

In some embodiments, waveform charge per phase (e.g. amplitude, waveform shape and/or pulse-width) can be controlled to selectively modulate and recruit neurons of differing diameter, conduction speed, and type (e.g., myelinated and unmyelinated).

In some embodiments, systems and methods can incorporate a variety of waveform frequencies, including high frequencies, e.g., about 1.2-50 kHz or higher; conventional frequencies, e.g., between about 20-1.2 kHz; low frequencies, e.g., between about 1-20 Hz; and ultra-low frequencies, e.g., below about 1 Hz. As noted elsewhere herein, direct current as defined herein is inclusive of low frequency AC current waveforms that are perceived as and functionally are direct current from the perspective of the tissue whose action potentials are being modulated.

A signal that averages a non-zero current over the duration of stimulation can include, for example, a charge imbalance, including but not limited to an intraphase bias, phase-to-phase bias, a cycle-to-cycle bias, an intermittent bias or offset, or any combination thereof. The bias may also be configured to be time-varying independent of the stimulation waveform.

In some embodiments, systems and methods can include pre- or post-conditioning before or after quasi steady-state stimulation. This can be important to, for example, limiting or ramping the voltage change rate so as not to invoke undesired electrode chemical reactions; slowly transitioning voltages or currents between on and off states to limit neural recruitment changes that can result in patient discomfort or off-target effects; and/or manage charge on, or voltage across, the electrode surface by effectively time shifting especially in the case of bipolar/multipolar where it can be desirable that waveforms on each electrode start and stop on cathodic cycles. Pre/post conditioning can allow an effective time-shift and ramp.

In some embodiments, systems and methods can include in vitro or in vivo preconditioning of electrodes using cyclic voltammetry or electroplating techniques. These can be used, for example, to remove electrode material defects in a controlled fashion to not overstress defect areas with high current densities and cause expansion rather than removal of defects. For example, a sharp point or edge on the surface of an electrode can generally have a higher current density relative to the rest of the electrode surface. This may lead to metal dissolution and formation of undesirable chemical species that may in that particular area accelerate electrode degradation. By etching away sharp edges in a controlled fashion, e.g., in vitro, the process can be directly controlled. Preconditioning can also be utilized for material deposition or controlled electrochemical conversion (e.g. formation of a protective oxide layer). Oxide growth can also be used to increase the charge capacity of the material, e.g., activated iridium oxide (AIROF) as one example.

Some embodiments can utilize AC and/or DC neuromodulation (e.g., stimulation or block) signals. AC signals can be used, for example, to include action potentials; paresthesia; and/or disable neurons to block neural signals.

In some embodiments, DC (including ultra-low frequency stimulation) can be utilized in addition to blocking action potentials to allow for superposition of an electric field across neurons for the purposes of inducing a transmembrane potential that can allow modulation of one or more of the following neuronal properties: Spiking properties; Excitability (increase or inhibit sensitivity); Conduction velocity; Control of electroporation; synchronization of neural populations; induction of secondary effects in cells that affect neighboring cells including vascular changes and blood brain barrier permeability; shift strength duration curve; DNA or RNA transcription or translation modification; and/or Protein or drug transport (electrophoresis).

In some embodiments, the electrode can comprise material(s) configured to optimize the charge capacity, durability, and biocompatibility, including, for example, any of: Iridium Oxide; Tantalum, MP35N, Titanium Nitride; Diamond; Boron-doped diamond; Nanotubes (e.g., TiN, $MnO_2$/

TiN); Metal Oxides (e.g., $RuO_2$, $IrO_2$, $MnO_2$, $CoO_2$, $NiO_2$, $FeO_2$, $SnO_2$ and $CuO_2$); Mixed Metal Oxides (e.g., $RuO_2$/SnO, $RuO_2$/NiO, $RuO_2$/$Ta_2O_5$, $RuO_2$/Pt, $RuO_2$/$TiO_2$, $RuO_2$/$MoO_3$, $RuO_2$/CaO and $RuO_2$/$V_2O_4$ or IrRu); Carbon/Graphene; metal carbides, carbonitrides and nitrides aka MXenes (or transition metal carbides, carbonitrides and nitrides); and/or combinations of any of the foregoing (including two or more metal oxides; two or more mixed metal oxides, a first material with a coating including the first material, and/or a second material, etc.).

In some embodiments, to increase the available electrochemical surface area (ESA), the substrate of an electrode may comprise microstructural features that increase the available surface area. In some embodiments, the substrate may comprise an open porosity sintered component. In some embodiments, the substrate may comprise an open porosity foam component such as a reticulate foam structure. In some embodiments, the substrate may comprise surface texturing from micromachining to generate features such as grooves or roughness to increase the overall ESA. These micromachining tools may comprise laser ablation to generate channels or grooves or general surface roughness. Additional micromachining techniques which can accomplish these goals are electric discharge machining (EDM), material etching techniques, pattern masking and etching techniques, bead or grit blasting, and surface sanding. The ESA can also be increased by, for example, electrophoretic deposition (EPD); electrolytic deposition (ELD); and/or electroplating. The substrate material can, for example, be coated with a high charge capacity material such as sputtered iridium oxide (SIROF), Poly(3,4-ethylenedioxythiophene)-poly (styrenesulfonate) (PEDOT), titanium nitride (TiN), fractal titanium nitride, porous titanium nitride, or some combination thereof. Methods for depositing such coatings on compatible substrates may include chemical vapor deposition (CVD) and physical vapor deposition (PVD). Substrates may comprise electrically conductive materials to allow for ease of charge transfer to the coating.

In some embodiments, systems and methods can include a physical set of electrodes and the pathways of which the stimulation can be delivered. Borrowing from electrochemical cell terminology, in some embodiments, a system can include N working electrodes (WE) tied to individual lead electrode contacts, one or more Indifferent Electrodes (IE), and optionally one or more Reference Electrodes (REF) if desired to measure half-cell potentials. The counter electrode (CE) can either be assigned to a WE or IE depending on the stimulation modality.

In some embodiments, measurement of electrode potentials can include voltages across any two of the electrodes (e.g., WE, CE, IE and REF) when stimulated with a known current. These measurements can be used to measure and track characteristics of the electrode including the impedance and capacitance of the electrode statically or dynamically during stimulation to assess the condition of each electrode and the system in general.

In some embodiments, any unstimulated electrode (e.g. electrode on the lead) may be assigned to operate as a REF and measure voltages/impedances based upon physical location to image and characterize physiological tissue. Any number of, or all of the electrodes can be switched between states, e.g., a reference electrode can be transformed into a working electrode, and a working electrode can be transformed into a reference electrode based on the phase of the stimulation pulse. In some embodiments, the WE or REF can be interchangeable depending on necessary current delivery (e.g., electrical conduction block with one segment, e.g., half of lead and a subsequently created block with another segment, e.g., half of lead to target different regions, and other examples).

In some embodiments, stimulation modalities include the following: monopolar where the current is driven through a lead electrode contact (WE) with positive and negative pulses of current and sinked by one or more indifferent electrodes; DC or similar current injection (bias) affected by shifting the waveform positive or negative; Bipolar where the current is driven with opposite polarities onto a pair of lead electrode contacts operating alternatively in the WE and CE roles, and any imbalance will be absorbed by one or more IEs; DC current injection (bias) affected by shifting each waveform positively or negatively and the difference can be absorbed by the IE(s); multipolar where the current is driven with opposite polarities onto a set of lead electrode contacts operating alternatively in the WE and CE roles. Any imbalance will be absorbed by the IE(s); and/or DC or similar current injection (bias) affected by shifting each waveform positively or negatively and the difference can be absorbed by the IE. Stimulation current outputs can be realized in some embodiments with the following mechanisms: Bipolar power supplies where current sources are driven by the positive supply and current sinks are driven by the negative supply providing unconstrained simultaneous positive and negative currents and the IE is tied to the Ground (0 V); and/or a monopolar power supply where a current source and sink are put in series and the a virtual ground develops between the two supplies.

In some embodiments, directly controlling electrode surface voltages during simultaneous stimulation can require additional techniques since the interaction between all the elements is related. This can be addressed, for example, in the following ways: In the case of simultaneous stimulation periodically turning off current to all but one electrode pair and making measurements at that time; Shifting phase between electrode pairs and making measurements when other pair(s) crosses zero current; utilizing reference electrodes located in proximity to the driven electrodes to that are to be measured; Limiting using worst-case voltages from the electronic current sources at the expense of not deriving all the performance of each electrode; control using voltages rather than current sources (voltage clamping), and/or control by using injected currents rather than voltages (bias currents).

In some embodiments, systems and methods can include electrode restoration techniques, including but not limited to Periodic Restoration—drive voltage/current to reset electrochemical surfaces, e.g. by periodically delivering a cathodic charge to drive down electrode voltage; and/or Adaptive Restoration—cycle by cycle drive voltage/current to preserve electrochemical surfaces, e.g. by dynamically adjusting the charge driven through the electrode to control electrode voltage.

In some embodiments, compliance voltage limiting can be utilized as an automatic way to limit chemical reactions (e.g. by setting compliance voltage such that there is enough voltage to drive the current sources and safe chemical reactions, but not enough voltage to provide electrode voltages sufficient to drive undesired reactions). In some embodiments, compliance voltage tracking can be utilized to reduce power dissipation. Current sources and sinks can be used to control current, and a switching variable power supply can generate just enough voltage to keep current sources and sinks in compliance, e.g., to supply the requested current. An alternate topology can be a variable voltage source to drive a specified current. One advantage of compliance tracking is that the current sources using MOSFET gate ratios (e.g. Wilson current sources) are inherently stable.

In some embodiments, driving voltage levels can be limited between pairs of electrodes as a means to limit chemical reactions or stop an electrode that is degrading and requires a higher driving voltage to deliver the target stimulation current.

In some embodiments, high frequency stimulation can be biased with a low frequency signal to reduce onset effects.

In some embodiments electrodes may comprise materials on which reversible electrochemical reactions can occur such as platinum which forms a hydride complex on its surface in aqueous solutions. To generate more surface area for reversible electrochemical reactions to occur, traditional electrodes and electrode materials may be made from high surface area to volume structures such as electroplated surfaces, (e.g., platinum black/electrodeposited iridium oxide for example), roughened surfaces, woven surfaces, patterned surfaces, reticulated foam structures, porous sintered bead structures, nano- or micro-patterned structures to expose additional material surface area. High-charge chemistry electrodes can be biocompatible, or suitably sequestered from body tissue if not. In some embodiments, the electrode driving current may be between about 0 mA and about 1 mA, between about 1 mA and about 2 mA, between about 2 mA and about 4 mA, between about 4 mA and about 8 mA, higher than about 8 mA, about 0.5 mA, 1 mA, 2 mA, 3 mA, 4 mA, 5 mA, 6 mA, 7 mA, 8 mA, 9 mA, 10 mA, or ranges incorporating any two of the foregoing values. In some embodiments this driving current is then used to generate a corresponding ionic current of similar magnitude, depending on the specific reversible electrochemical reactions.

Some embodiments can include a material such as tantalum or titanium nitride to generate a capacitive traditional electrode interface instead of an interface at which an electrochemical reaction occurs. Transparent conducting oxides (TCOs) such as fluorine-doped tin oxide (FTO), nickel titanium dioxide (Ni/TiO2), and other titanium dioxide (TiO2) constructs are also candidate materials that have high charge carrying capacities, as well as others disclosed herein. In some embodiments, the electrodes can include tantalum coated with titanium nitride. In some embodiments, the electrodes can include MP35N coated with titanium nitride. In some configurations, charge generation at the traditional electrode surface would attract ionic species from the ionically conductive material until the charge at the traditional electrode interface is passivated. Charging of the capacitive material with an electric current of one polarity can generate current flow in the form of ions. Reversing the polarity of the current flow to the capacitive material can effectively reset the system for a subsequent charging to generate further ionic current flow. To generate more surface area for increased ion current flow capacity to occur, traditional electrodes may be made from high surface area to volume structures such as roughened surfaces, reticulated foam structures, porous sintered bead structures, nano- or micro-patterned structures to expose additional material surface area. In one embodiment, this capacitive structure is in fluid contact with an electrolyte solution that contacts an electrolyte-saturated hydrogel in contact with target nerve tissue to enable ion current flow to the tissue. In some embodiments, the solution is body fluid such as interstitial fluid that delivers the current to the electrically excitable tissue from the electrode.

To deliver current to the nerve to facilitate a block, the electrode may be connected via a conductive lead to one or more current sources. A single nerve-electrode interface can provide nerve block when current is applied in one polarity (blocking phase). When the current polarity is reversed to return the electrode to its original state (which may be a non-blocking phase or also a blocking phase), the nerve may or may not continue to block pain stimulus from passing along the nerve. If the nerve has been placed into a state of hypersuppression, the nerve will continue to prevent action potential propagation and block pain signals regardless of the phase state of the electrode. However, if the nerve is not placed into a state of hypersuppression, the nerve may pass undesirable signals when the blocking-phase signal in absent. Fridman and Santina have described a means to enable continuous block when current polarity is reversed such that the neural tissue see a constant current while each driving electrode experiences an alternating current (AC) using a series of valves to direct current flow direction (Fridman and Santina, Safe Direct Current Stimulation to Expand Capabilities of Neural Prostheses, IEEE Transaction of Neural Systems and Rehabilitation Engineering, 2013 March 21(2):319-328; Fridman and Santina, Safe Direct Current Stimulator 2: Concept and Design, Conf Proc IEEE Eng Med Bio Soc, 2013: 3126-3129). However, in some cases it is desirable to have a simpler system which does not require the use of valves which present additional failure points and add bulk to an implantable system. A simpler, more robust system may be configured without valves and such moving parts by using multiple electrodes to provide constant stimulation of the nerve tissue itself. In one embodiment to provide continuous block, two nerve-electrode interfaces are present and connected to one or more current sources. The first nerve-electrode interface electrodes is run with the current in one polarity to drive a block while the second nerve-electrode interface is run with the opposite polarity. After a period of time, the current polarities of the first and second electrodes are reversed, and the second nerve-electrode interface provides a block while the first nerve-electrode state is reversed to its prior state. By cycling the electrode currents, a continuous block can be maintained at the target nerve. As can be appreciated, more than two, such as 3, 4, 5, 6, 7, 8, 9, 10, or more electrodes may also be used to facilitate the same continuous block. Electrodes may also be run in either monopolar or bipolar configurations. In some embodiments the electrodes system is configured to not have any actuated mechanically moving parts such as valves or hinges.

Alternatively, nerve activity may be suppressed which means that nerve activity remains blocked or reduced even after removal or discontinuation of the blocking current. The nerve may be further put into a state of hypersuppression in which the nerve remains blocked or reduced in activity without rapid reversibility after cessation of DC delivery. Modulation of the initial current delivered to the nerve tissue including ramp rate, current amplitude, total charge delivery, and waveform shape can be used to place the nerve in a state of suppression. During the state of suppression, the electrodes may be returned to its initial state by reversing the current polarity used to generate the initial block and suppression state. During the period of reverse current flow, the nerve may remain in a state of hypersuppression. In another configuration the system may deliver subsequent blocking or activity reducing current inputs that extend the suppression duration, with periods of no current delivery, or of reversal current in between current doses. The nerve tissue may remain in a state of hypersuppression during the periods of non-blocking or non-activity reducing current input. In another configuration, the system may be configured to deliver subsequent current inputs on a schedule. In some embodiments, the DC blocking or activity reducing waveform may have an amplitude of between 0-250 microamps, 250-500 microamps, 500-1000 microamps, 1000-1500 microamps, or 2000 microamps, or higher, or about, at least about, or no more than about 50, 100, 150, 200, 300, 400, 500, 600, 700, 800, 900, 1,000, 1,100, 1,200, 1,300, 1,400, 1,500, 1,600, 1,700, 1800, 1,900, 2,000, 2,500, 3,000, 3,500, 4,000, 5,000 microamps or more, or other ranges incorporating any two of the aforementioned values. Placing a nerve into a state of hypersuppression may be facilitated in some embodiments by delivering a charge of 1-2 millicoulombs, 2-5 millicoulombs, 5-10 millicoulombs, 10-50 millicoulombs, 50-100 millicoulombs, 100-500 millicoulombs, 500-1000 millicoulombs, or 1000 millicoulombs or greater, or about, at least about, or no more than about 1, 2, 5, 10, 25, 50, 100, 200, 300, 400, 500, 600, 700, 800, 900, 1,000, or more millicoulombs, or other ranges incorporating any two of the aforementioned values, and depending on nerve size and desired hypersuppression duration. Activity reducing amplitude and current duration may be tuned to enable hypersuppression in the range of, for example, 0-0.5 times the duration of initial blocking or activity reducing waveform delivery, 0.5-1 times the duration of initial waveform delivery, 1-1.5 times the duration of initial waveform delivery, 1.5-2 times the duration of initial waveform delivery, and greater than 2 times the duration of initial waveform delivery, or about, at least about, or no more than about 0.1×, 0.2×, 0.3×, 0.4×, 0.5×, 0.6×, 0.7×, 0.8×, 0.9×, 1×, 1.1×, 1.2×, 1.3×, 1.4×, 1.5×, 1.6×, 1.7×, 1.8×, 1.9×, 2×, 2.5×, 3×, 4×, 5×, or more relative to the duration of initial waveform delivery, or ranges including any two of the aforementioned values.

Sensing the local state of and proximal to the nerve tissue can also provide a useful measure for determining when to provide current inputs to extend nerve suppression as well as to provide a feedback loop for initial current delivery to generate the initial nerve block by modulating the nerve potential such that it cannot transmit action potentials. In one embodiment the nerve's ability to conduct action potentials is monitored such that as direct current is delivered to the nerve tissue, the direct current delivery can be maintained to ensure that the nerve block is maintained, for example. Nerve conduction ability may be monitored by any suitable measure such as delivering a stimulus pulse and measuring compound action potential signals.

In some embodiments sensing is in the form of a reference electrode to measure potential differences relative to the two electrodes which are passing the active current. In some embodiments the active current is modulated in response to one or more measured electrode potentials relative to the reference electrode. In some embodiments the active current is modulated when measured electrode potential indicates that undesired electrochemical reactions may occur at one or more active electrodes. For example, active current may be reduced or ceased upon measurement of an active electrode potential that indicates water electrolysis is occurring or possible. The system may be operated with a direct current input or by applying a potential difference between the working electrode and an auxiliary or counter electrode. In some embodiments, a reference electrode may be located within the system or at the distal end of the system proximal to the nerve tissue.

Using these methods of placement of blocking or activity reducing electrodes along the spinal column to modulate activity in the spinothalamic tract and the ability to tune the electric field to generate nerve block or activity reduction and/or suppression, specific targets for pain attenuation can be facilitated. For example, trunk pain which is moderated by the thoracic vertebral levels can be modulated by placing leads along the thoracic spine while neck pain may be moderated by providing block or activity reduction and/or suppression in the cervical spine. Upper limb pain may be moderated by providing a combination of cervical and thoracic level block or activity reduction and/or suppression while lower limb pain may be moderated by a combination of lumbar and sacral level block or activity reduction and/or suppression in the spine.

Generation of pain block or attenuation can be used to facilitate peri-procedural pain block where motor control and non-pain sensations are desired. For example, in labor and delivery of a child, one of the challenges with pain management particularly with epidural anesthesia is the reduction in ability to be sensate in the lower body. Due to the non-specific nature of the delivered anesthesia in the epidural space sensory, pain, and motor neurons are impacted. The epidural anesthesia can lead to difficulty with generating pushing force during the birthing process and can lead to numbness a few hours after birth impairing motor abilities such as the ability to walk. In some instances, epidurals are further implicated in fetal and newborn health including breastfeeding difficulty. Using the blocking electrodes described above to target the spinothalamic tract and/or dorsal root ganglia, the undesired pain can be targeted without generating the side effects (or reducing side effects) associated with current epidural anesthesia techniques because only the pain tracts are targeted and not any other motor or sensory tracts. Furthermore, in the case in which ionic current is delivered to the nerve tissue in a reversible blocking fashion, the stopping of block can enable the patient to immediately be restored to normal pain sensation if desired and any off-target block can be reversed enabling immediate body function restoration.

Beyond central nervous system interventions, a safe direct current block or activity reduction can also be facilitated in the peripheral nervous system in which electrodes are placed in contact or in proximity to peripheral nerves to facilitate block or activity reduction. Specific pain targets include, for example, focal pain, phantom limb pain, neuroma pain, and neuralgias. A pain target could also include post-operative pain. Targeting the peripheral nerves proximally (i.e. closer to the spinal cord) from the site of pain for block or activity reduction can suppress pain from the distal site. Specific to neuralgias, postherpetic neuralgia (after shingles) can be targeted based on the presentation of the outbreak which will trace specific dermatomes. For trigeminal neuralgia, the trigeminal nerve (and/or trigeminal ganglion and/or trigeminal nucleus in the brainstem) can be targeted for block to reduce pain that commonly manifests as facial pain. Another target is the glossopharyngeal nerve which produces pain in the neck and throat. Neuralgia in extremities such as the hands, arms, feet, and legs as frequently caused due to diabetes-related neuropathies are also potential targets.

In some embodiments, electrical neuromodulation of tissue including delivery of high charge densities via an ultra low frequency waveform and use of at least one indifferent electrode to absorb a bias current can unexpectedly, advantageously, and safely enable continued suppression of neural activity after cessation of current delivery (wash-out period), which can provide multiple benefits. For example, power can be saved or, stated differently, power consumption can be slowed. In another example, the sudden return of neural activity can be prevented in case of device failure (e.g., connection, battery, etc.), which can improve safety and/or enable patient/physician intervention during prolonged suppression period. Similarly, the rapid return of pain in the event of device failure and/or the rapid return of sympathetic signaling that may lead to acute sympathetic events (such as acute decompensation or cardiac arrhythmias) can be prevented. In yet another example, when implemented as an electronic medicine dosing system/method, a long-lasting therapeutic benefit can be created from acute application. Furthermore, such systems and methods can be very safe, inhibiting/minimizing the creation of toxic species at the electrode-nerve interface.

In some embodiments a system is configured for generation of nerve block or activity reduction for disorders and diseases that can be addressed by reducing neural activity in specific regions of the brain responsible for the specific disorder. Neural activity reduction can be facilitated by directly blocking and/or reducing activity of specific neurons as well as by blocking pathways along which excessive neural signaling is occurring. In some embodiments, this system for deep brain block (DBB) comprises all or some of the steps of identification of the anatomic target site for block, creating an access site to the exterior of the brain tissue, creating a path through the brain tissue to the target site, evaluating the suitability of the target site for block, adjusting or refining the location of the target site, providing nerve block at the target site, and adjusting the nerve tissue block strength or location. Practically, this process may be implemented using techniques known in the field of deep brain stimulation (DBS) in which a target anatomic site is identified using a combination of imaging techniques such as but not limited to magnetic resonance imaging (MRI) including functional MRI (fMRI), computed tomography (CT), PET scanning, and/or x-rays. This site can then be accessed using stereotactic techniques to register an identified region from imaging to the physical anatomy on the patient. A frame may be fixed to the patient's head and skull to allow for spatial registration during the procedure. An access site to the brain tissue in the form of a burr hole or craniotomy can be formed with or without additional access tools fixed to the skull such as insertion cannula and advancement/retraction equipment to access the target site. Advancement of a nerve tissue activity measurement probe through the brain tissue to the target site may be used to enable evaluation of the suitability of the brain region. This probe may record neural activity to determine that the measured signals are consistent with that of tissue requiring block or activity reduction. If the signal characteristics indicate that the location is not optimal or appropriate for block or activity reduction, the probe may be adjusted until the correct location is identified. The measurement probe may be exchanged with the therapeutic electrode which can then be inserted with the active portion of the electrode positioned within the target site. Activation of the blocking or activity reducing signal can then be used to assess efficacy of the block as well as to tune the strength of the signal. The therapeutic electrode can then be fixed to the skull to maintain the active portion's (e.g., region delivering ionic current) position at the target site. An extension lead can be connected to the affixed therapeutic electrode and connected to an implantable current source, similar to an implantable pulse generator (IPG), whose output signal can be adjusted to facilitate optimal symptom reduction. Blocking or activity reducing electrodes may be implanted unilaterally or bilaterally as the contralateral side of the body is affected by specific anatomic target sites.

Disclosed herein in some embodiments are systems and methods to limit undesired electrochemical reactions by monitoring signals indicative of conditions favorable for such reactions to occur and modification of the reaction generation conditions. Not to be limited by theory, traditional alternating current stimulation of neural tissue typically delivers a relatively low amount of charge through conventional electrodes (e.g., platinum electrodes). However, in some embodiments, high charge density electrodes including those described elsewhere herein deliver relatively greater amounts of charge closer to and beyond, and in some cases far beyond, the Shannon limit. Control systems and methods such as those disclosed herein can surprisingly and advantageously allow for the safe delivery of such current to tissue.

In some embodiments, a system can include a monitoring system, e.g., including a hardware and/or software controller configured to measure the voltage required to generate the electric current to drive the stimulation current. If the voltage crosses a threshold, e.g., a predetermined threshold, the controller can adjust (e.g., increase or decrease) the current output to bring the voltage level into an acceptable range relative to the threshold voltage level. For example, if the voltage required to maintain a specific current level becomes too high, the current level may be reduced to the point that the voltage falls below the defined threshold. In some embodiments, if the voltage required to maintain a specific current level becomes too high, the current level may be set to zero. In yet another alternative system, if the voltage required to maintain a specific current level becomes too high the current level may be reversed.

In some embodiments, the current may take the form of a waveform such as, for example, a square wave or other arbitrary shape in which current is passed between the two electrodes with opposite polarity. The voltage waveform required to drive the current between the electrodes may fall within an upper and lower voltage threshold limit. Over time, if the underlying electrode charge capacity is found to change because of various conditions, the driving voltage waveform required to maintain the target current waveform may also change. If the excursions/deviations from the target thresholds are significant enough, this may be indicative of undesired electrochemical reactions occurring. The voltage threshold limits and associated voltages may alternatively or additionally be measured between the working electrode and reference electrode to directly assess the voltage drop across the working electrode-electrolyte interface to assess the propensity for undesirable electrochemical reactions and voltage potentials across that interface. In some embodiments the voltages between two or more working electrodes may be used to assess electrode status. In some embodiments the voltages between a working electrode and indifferent electrode may be used to assess electrode status. To prevent these excursions into undesirable zones, the current delivered may be adjusted to reduce the driving voltages as described above. Alternatively, the voltage excursions may be due to changes in electrochemistry. For example in a system in which a reaction occurs where the same target amount of charge is transferred from one electrode to a second electrode and back to the first electrode, the net charge over time may drift from zero (e.g., become unbalanced) due to imperfect charge accounting. This in turn may lead to changes in voltage required to generate the desired current and be indicative of undesired electrochemical reactions occurring. The drift in net charge transfer from a target level may be countered in some embodiments by monitoring the driving voltage and generating a control loop that generates additional charge on an electrode which has been detected via its driving voltage characteristics to be deficient in reactants. In other embodiments a bias current may be used to explicitly unbalance the charge transfer and drive the electrode operating voltage into a more cathodic or more anodic state.

In some embodiments, the electrode could have a working surface area of, for example, about, less than about, or no more than about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 90, 100 mm$^2$, or more or less, or ranges including any two of the foregoing values.

In some embodiments, the maximum electrode voltage limit could be, for example, about, less than about, or no more than about −0.3, −0.2, −0.1, 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8. 1.9, 2, 2.5, 3, 3.5, 4, 4.5, 5V, or more or less, or ranges including any two of the foregoing values.

In some embodiments, the peak-to-peak voltage limit could be, for example, about, less than about, or no more than about 500, 600, 700, 800, 900, 1000, 1100, 1200, 1300, 1400, 1500, 2000, 2500, 3000, 4000, 5000, 10000 mV or more or less, or ranges including any two of the foregoing values.

In some embodiments, the voltage variation limit could be, for example, about, less than about, or no more than about 0.1, 0.5, 1, 5, 10, 15, 20, 25, 50, 75, 100, 125, 150, 175, 200, 225, 250 mV, or more or less, or ranges including any two of the foregoing values. Voltage variations can be measured over durations such as minutes, hours, or days, for example.

In some embodiments, the time period limit could be, for example, about, less than about, or no more than about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 120, 200, 500, 1000, 5000, 10000 seconds or more or less, or ranges including any two of the foregoing values.

In some embodiments, such as in the algorithms disclosed, for example, the electrode can be conditioned in a manner that allows for delivery of the target current amplitude for the desired duration with a driving voltage below a set threshold such as the electrolysis potential, for example. The algorithm also limits the amount of time the electrode is exposed to voltages above the driving voltage upper threshold which can lead to generation of deleterious by products that can damage tissue.

In some embodiments, direct current (DC) delivery amplitudes for any therapy disclosed herein could be, for example, in the range of about 0 to about 0.5 mA, about 0.5 to about 1.5 mA and about 1.5 to about 2.5 mA, or ranges incorporating any two of the foregoing values. In some embodiments, about 2.5 mA to about 5 mA and about 5 mA, about 5 mA and about 15 mA, and above can be utilized both for anodic and cathodic current levels for block. Response has been seen, for example at about 0-1.5 mA range in animal studies as well as paresthesia onset in peripheral human nerves at about 1.5 mA (cathodic and anodic) with complete block at about 2.5 mA and current delivery up to about 5.5 mA. Therapeutic values for pain relief have been seen in the spinal cord in, for example, the 0.5-1.5 mA range, or about, at least about, or no more than about 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 mA, or more or less, or ranges including any two of the foregoing values.

In some embodiments, direct current delivery to a patient can be targeted to any number of anatomical locations, including but not limited to: the dorsal root ganglion; dorsal roots; dorsal columns; dorsal horn; Lissauer's tract; and/or the antero-lateral pain tracts. In the spine, the stimulation delivery can be targeted to any number of vertebral levels including but not limited to the sacral region, the lumbar spine, the thoracic spine, the cervical spine as well as over specific spinal disk locations such as, for example, any number of disks between any two of C2, C3, C4, C5, C6, C7, T1, T2, T3, T4, T5, T6, T7, T8, T9, T10, T11, T12, L1, L2, L3, L4, L5, S1, S2, S3, or S4, including but not limited to the disk bridging the T9 and T10 vertebra. In some embodiments, direct current delivery can be directed to a peripheral nerve, or other target locations as described elsewhere herein. Not to be limited by theory, in some embodiments DC delivery can potently modulate small diameter fibers in the spinal cord and depolarize spinal cord neurons. DC delivery may not necessarily be sensitive to fiber size and may have a wide therapeutic window. DC delivery can be utilized for a wide variety of indications, including but not limited to cardiac mapping for arrhythmias, epilepsy, and movement disorders, as well as a variety of other conditions disclosed elsewhere herein.

The systems and methods described herein may be used to generate DC nerve block, modulation or attenuation. Depending on the specific direct current application of nerve block, nerve suppression, or continued block after removal or stopping of the current may occur, and hypersuppression may result for continued nerve blockade in excess of one minute after removal of the DC source to delay nerve conduction recovery. The nerve block and suppression may be generated in an intermittent or continuous manner depending on the desired application. Means for continuous nerve block have been described that provide for safe delivery of nerve block via ionic current utilizing multiple electrodes or sequenced electrode contact activation enabling a means to modulate nerve conduction safely without necessitating complex mechanical systems. The system may be fully or partially implantable, or completely non-implantable (e.g., transcutaneous) with all tissue contacting materials biocompatible for tissue contact and implantation compatibility.

Figure 1:
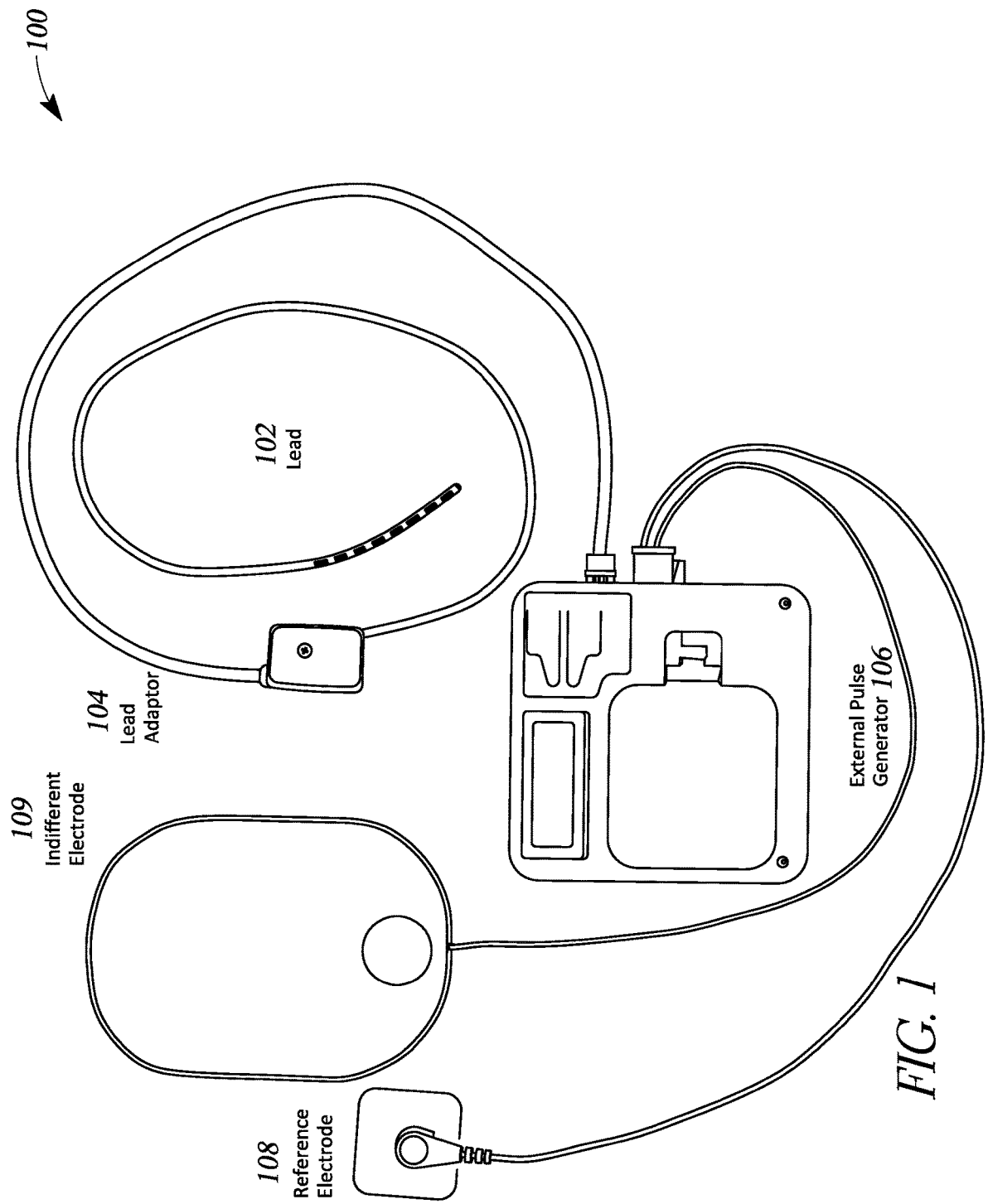
FIG. 1 schematically illustrates one non-limiting example of a neuromodulation system.

FIG. 1 schematically illustrates one non-limiting example of a neuromodulation system 100. The system can include any number of the following: 1) the Leads (one shown) 102, 2) the Lead Adaptor 104, 3) the External Pulse Generator 106, 4) the Clinician Programming Application (CPA)/Clinician Programming Device (CPD) (not shown); and 5) the Surface Electrodes (optional Reference 108 and Indifferent 109) 108.

Figure 2:
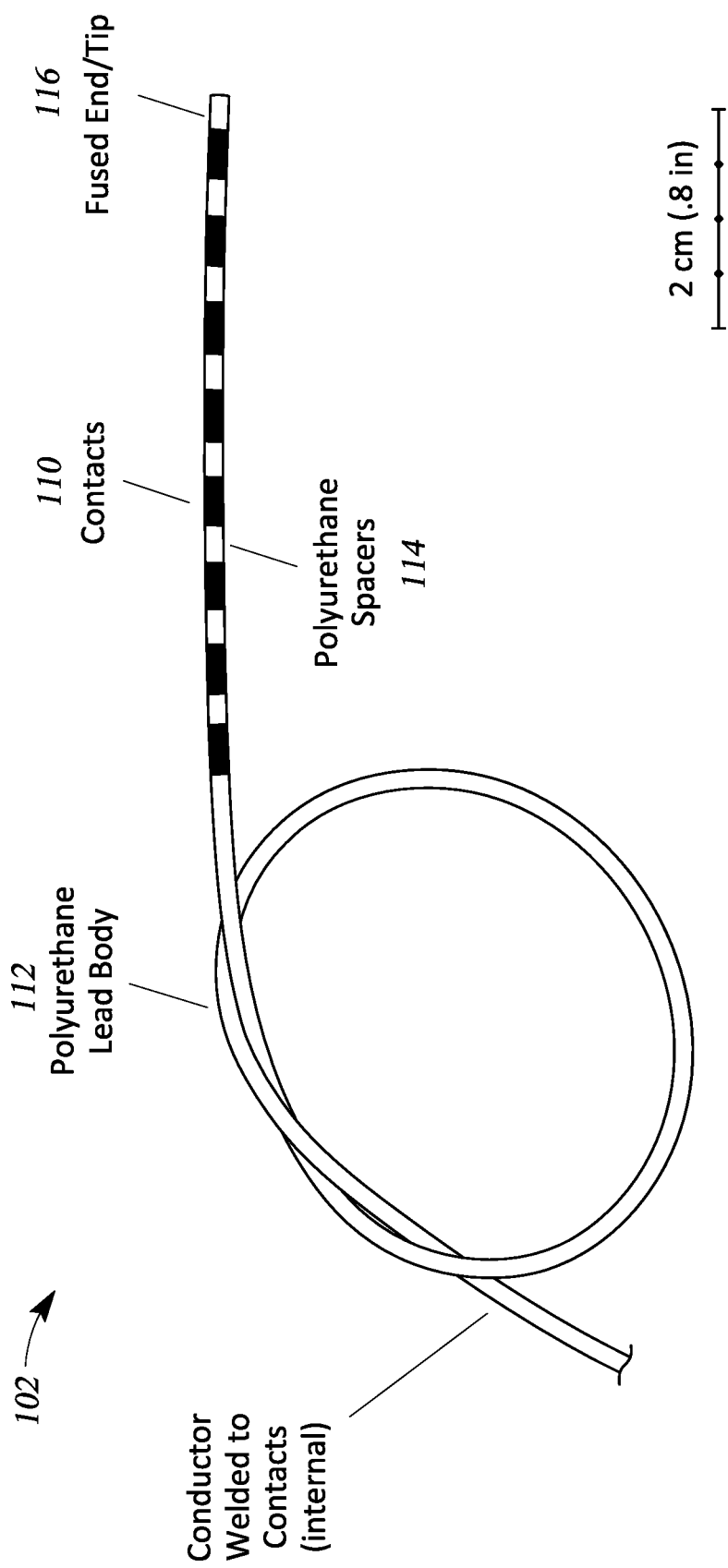
FIG. 2 schematically illustrates an embodiment of a percutaneous lead.

FIG. 2 schematically illustrates an embodiment of a lead 102, which can be, for example, an epidural lead. In some embodiments, a lead could have, for example, a diameter of between about 1 mm and about 2 mm, and can be an appropriate geometry, e.g., cylindrical in shape with up to eight individual contacts (or more) 110 occupying the distal working end. The lead may be, for example, 40-100 cm in length in increments of 5 cm or more or less in length. The individual contacts 110 can be made of a substrate coated with a high capacity charge coating, including but not limited to titanium coated with titanium nitride or other materials as disclosed herein for high capacity current delivery. Each contact 110 is welded to a conductor which may comprise, for example, platinum-iridium, MP35N, 35N LT, stainless steel: 304SS, 316LVM, or titanium wire which terminates in a connector. The conductors may also terminate in ring-style connector contacts such as Bal Seal style connectors. The lead body 112 itself can be made of medical-grade polyurethane. The lead 102 can include multiple lumens, at least one for each wire and at least one central lumen for the stylet, which is used for steering and increasing the column strength of the lead during insertion. One or more spacers 114, which can include polyurethane spacers, can be positioned between adjacent contacts 110. The lead 102 can terminated in a tip 116, which can be a fused end.

Figure 3:
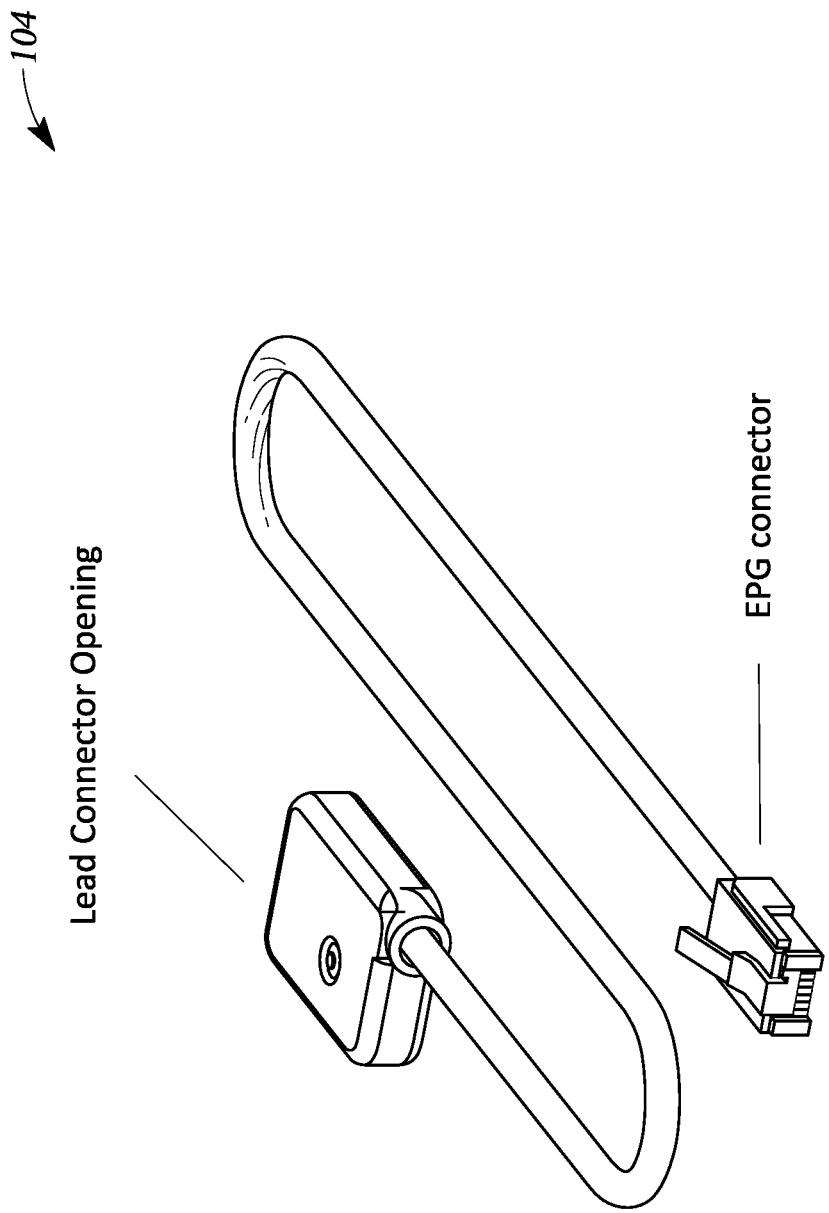
FIG. 3 schematically illustrates a lead adaptor, according to some embodiments.

FIG. 3 schematically illustrates a lead adaptor 104, according to some embodiments. The lead adaptor 104 mates the lead 102 to the EPG. The inside of each lead adaptor 104 can include a series of receptacles which accept the lead connector on the lead 102 to establish electrical connectivity with the EPG. The lead 102 is held in place using a retention system similar to those found in other SCS lead connector systems, comprising a clamping system and friction channel to secure the lead 102 to the lead adaptor 104. The lead adaptor case can include a communication, e.g., Ethernet or other type cable and connects the adaptor to the EPG.

Figure 4:
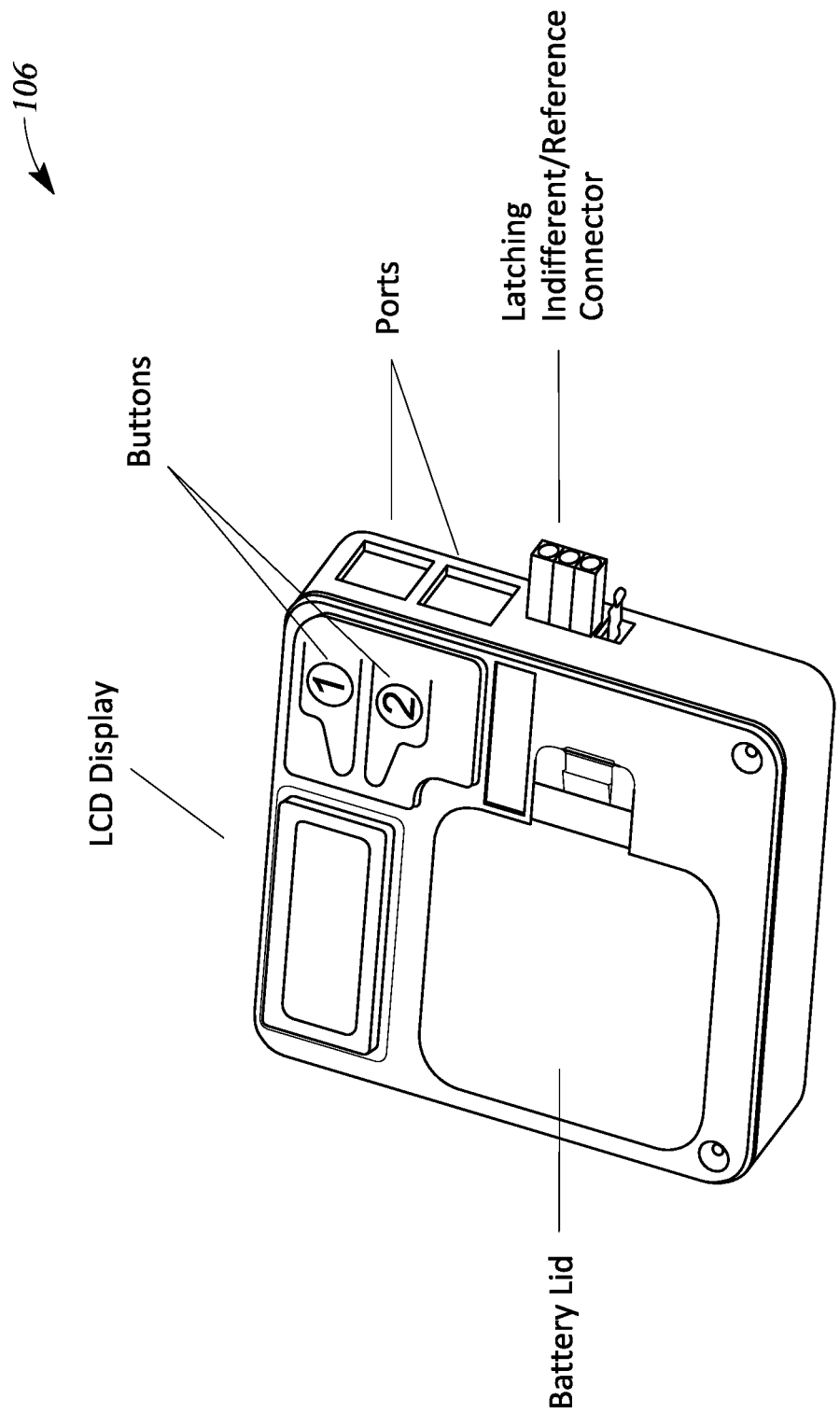
FIG. 4 schematically illustrates an external pulse generator (EPG), according to some embodiments.

FIG. 4 schematically illustrates an external pulse generator 106 (EPG), according to some embodiments. The EPG is the unit that generates the therapeutic pulses. It is a box made of nylon or other appropriate material as one non-limiting example. The percutaneous lead adaptor 104 interfaces with the EPG through connectors, such as two Ethernet-style or other connectors. The EPG power supply can be provided by, for example, four standard primary cell lithium AA batteries. Users can interface with the EPG via, for example, two buttons positioned next to an optional display, e.g., a LCD or other screen. The optional LCD displays the status of the device and battery status to the user. The user is given audible and/or visual alerts to prompt action for states which require the user's attention such as battery changes. Other visual indicators, such as, for example, LEDs visible through the EPG case or openings in the case provide additional indications to the user. The EPG is also connected to a skin surface indifferent electrode. The indifferent electrode is connected through connector on the EPG such as a latching connector. In some embodiments, an automated external defibrillator electrode was chosen as the indifferent electrode for well-established safety and low electrical impedance. Additionally, an optional external reference electrode can be available on the same harness. The reference electrode itself can be, for example, is a commercially available electrocardiogram electrode. The EPG can be programmable through a wireless connection to a Clinician Programmer Device (CPD) that is USB connected to a PC running the clinician programming application (CPA). Alternatively, the EPG may be directly connected to the PC via a direct USB or other cable connection. The EPG can normally reside, for example, in a belt-mounted holster type pouch that the patient will wear during use. In some embodiments, the system (including but not limited to the pulse generator) could be fully or partially implantable, and include, or not include any transcutaneous components, and/or be configured be controlled or interrogated with an external device.

Figure 5:
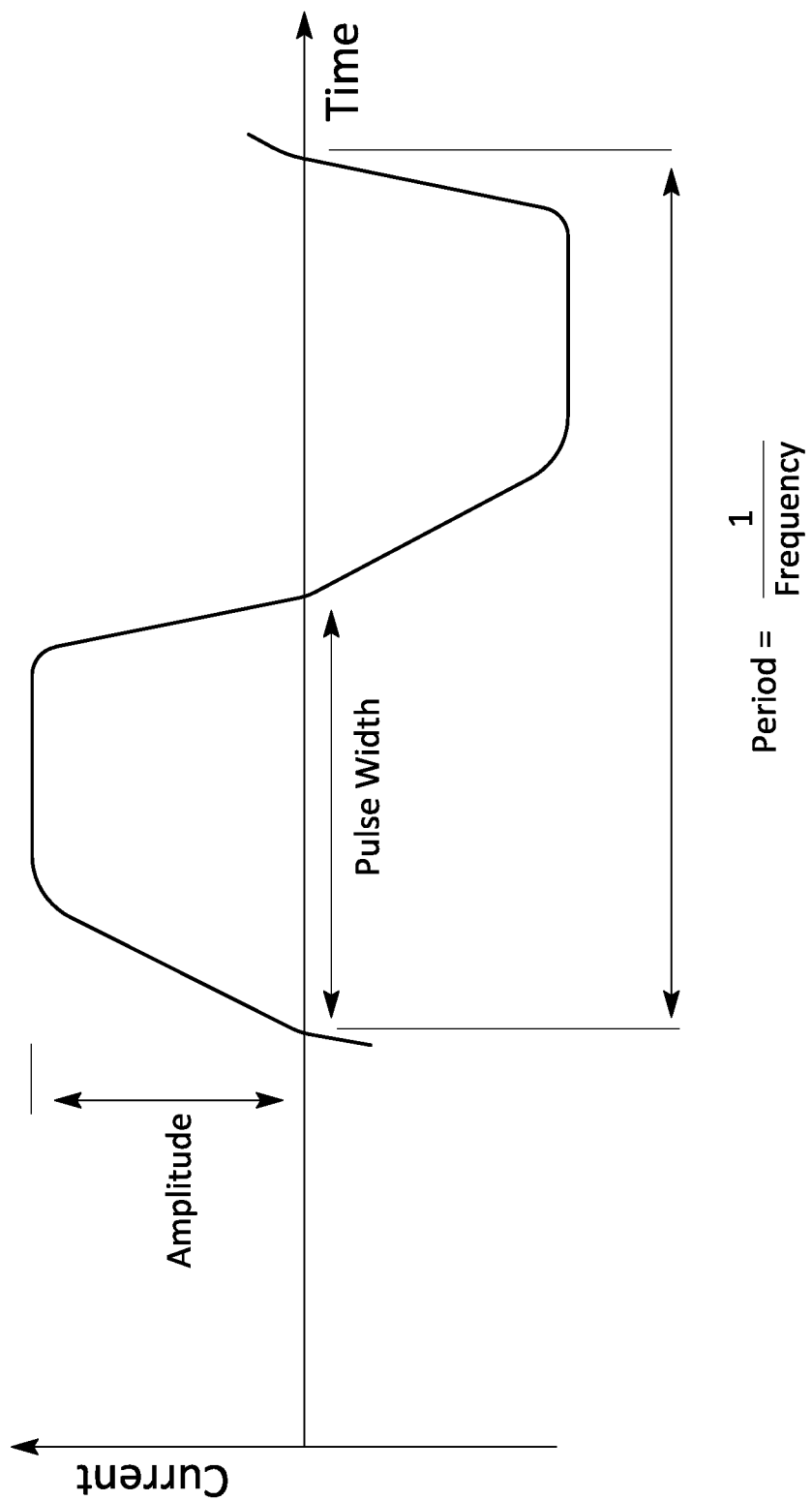
FIG. 5 schematically illustrates an example of an EPG Output Waveform.

FIG. 5 schematically illustrates an example of an EPG Output Waveform. The EPG outputs pulses which are ramped both up and down. The pulse width, frequency and amplitude can be programmed using the Clinician Programming Device. In some embodiments the EPG can output a current of between about 0-10 mA, or other values/ranges as disclosed herein (and is configurable to not exceed the electrode charge injection capacity). In some embodiments, the EPG has an output frequency of between about 0.05 Hz and about 2 Hz, or other values/ranges as disclosed herein. In some embodiments, the EPG waveform has a pulse width of between about 250 ms and about 30 seconds, or other values/ranges as disclosed herein.

Systems and methods can also include a Clinician Programming Application (CPA)/Clinician Programming Device (CPD). In some embodiments, a computing device with the Clinician Programming Application (CPA) communicates wirelessly with the External Pulse Generator via the Clinician Programming Device (CPD) which is attached via, e.g., USB to the computing device. The system uploads the waveform to the EPG based on the parameters set by the programmer/clinician. It also can have the capability to download logs and performance data from previous stimulation sessions.

Figure 6:
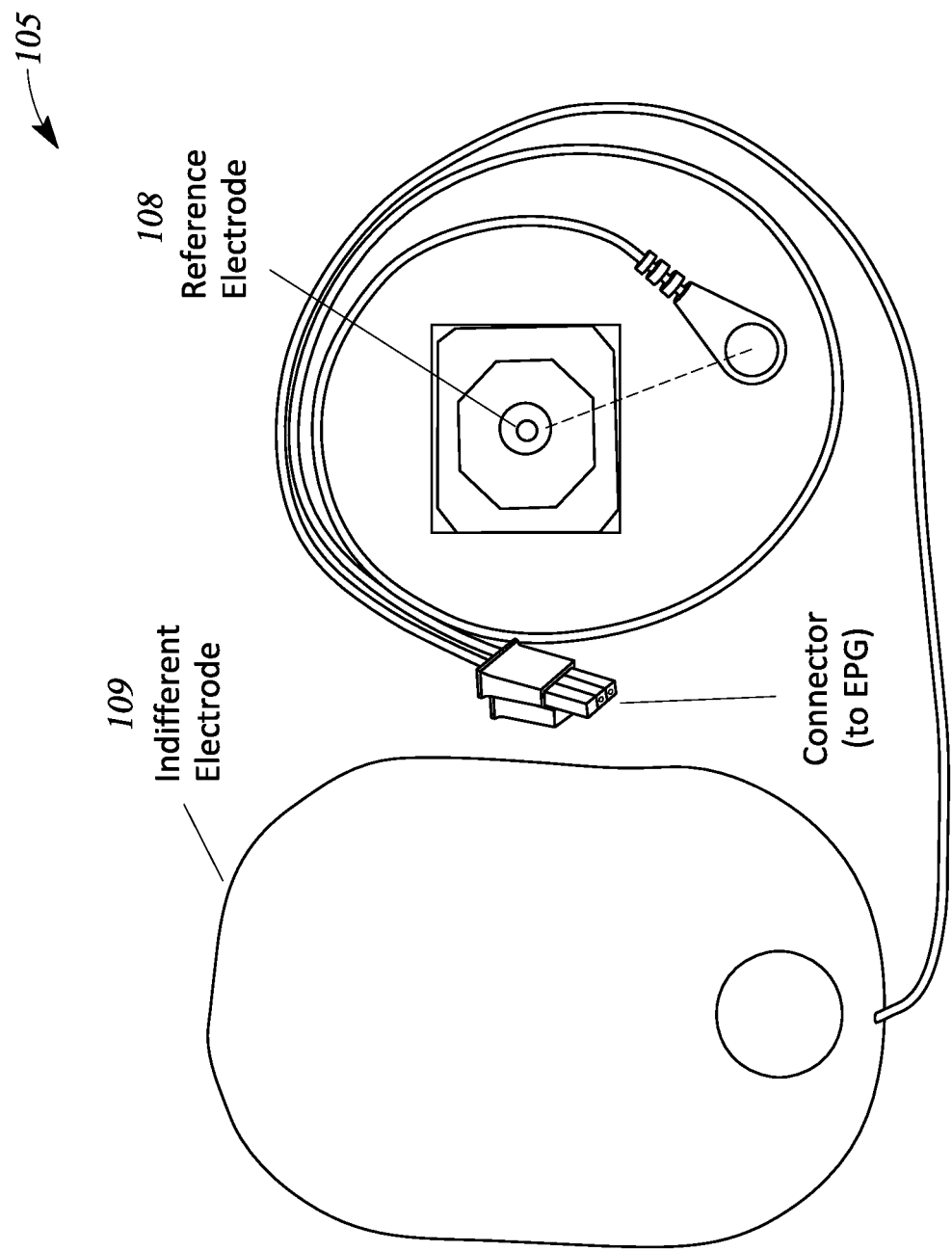
FIG. 6 schematically illustrates a surface electrode carriage device.

FIG. 6 schematically illustrates a Surface Electrode Harness 105, which can comprise an Indifferent Electrode 109 and a Reference Electrode 108, as well as a connector that interfaces with the External Pulse Generator. The electrodes can serve to enable delivery of the output waveform, specifically absorbing the bias current regardless of polarity, and recording of performance data. The electrodes can adhere to the skin and can be further secured with adhesive films such as, for example, Tegaderm as necessary.

Figure 7:
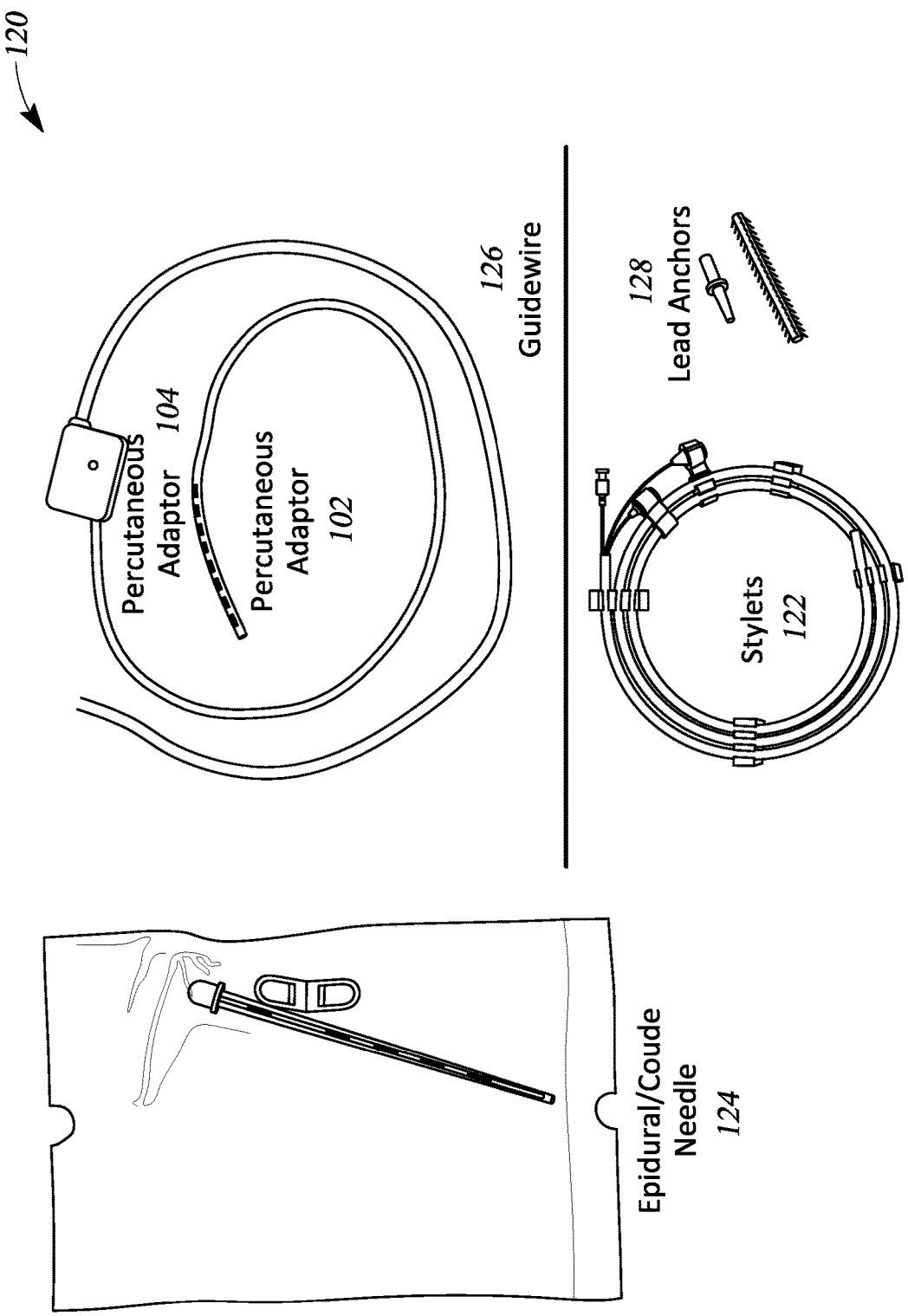
FIG. 7 schematically illustrates one embodiment of a sterile lead implantation kit.

FIG. 7 schematically illustrates one embodiment of a sterile lead implantation kit 120, which includes leads and lead adaptors, as well as any number of the following: leads 102 (1 shown); Percutaneous Adaptors 104 (1 shown); (3) Stylets 122 packaged in a round Teflon holder, one straight and two curved-tip stylets 122 of increasing stiffness; (2) Coude needles 124; (1) Epidural access guidewire 126; and (2) Lead retention anchors 128. Not shown is a tunneling tool for full lead implantation.

Figure 8B:
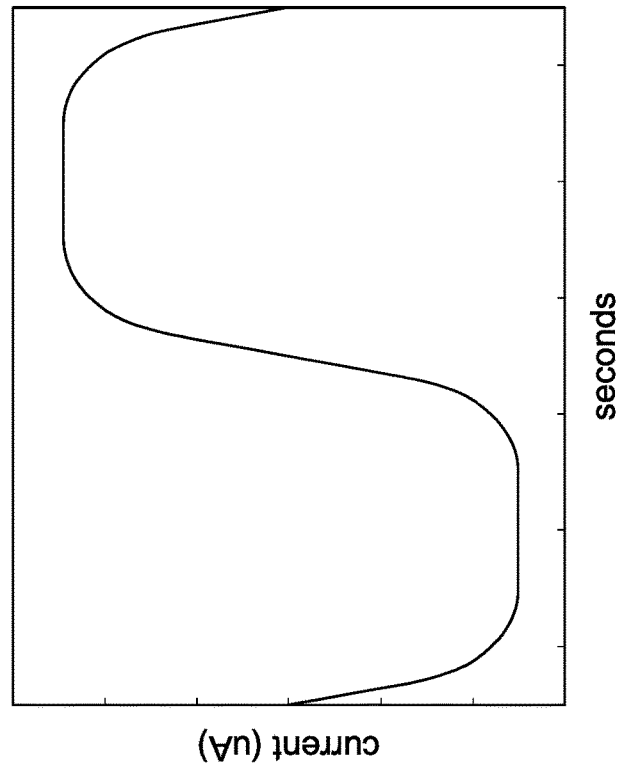
FIG. 8B illustrates an SCS waveform.
Figure 8A:
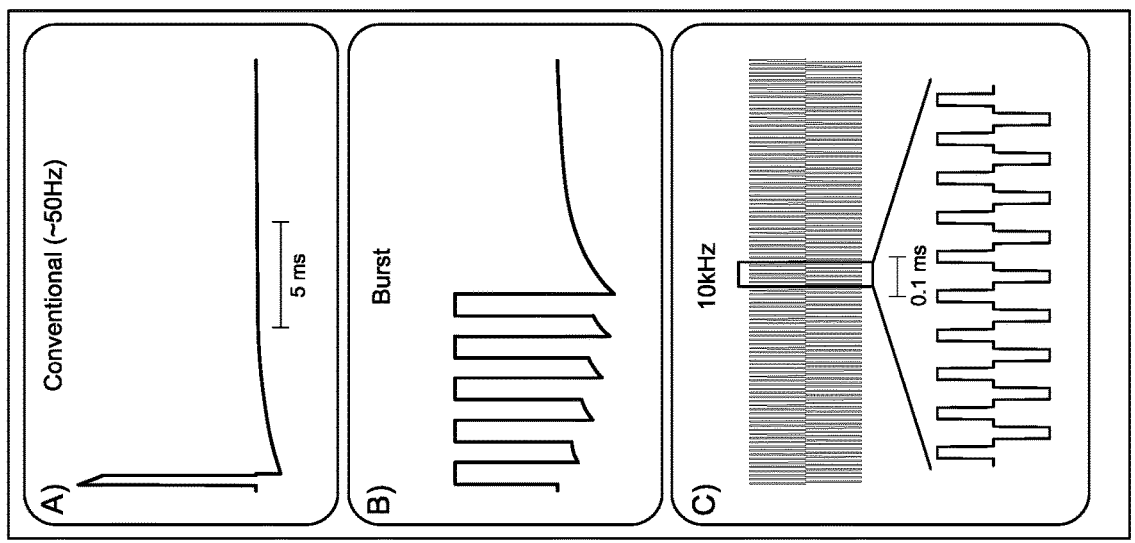
FIG. 8A illustrates spinal cord stimulation (SCS) waveforms.

FIG. 8A illustrates example spinal cord simulation (SCS) waveforms, including conventional, burst, and high frequency (e.g., greater than about 1 kHz, or more). As illustrated, each of the foregoing waveforms include sharp angles or corners. In contrast, the SCS waveform illustrated in FIG. 8B includes curves in place of sharp angles, corners, or edges, which can provide any number of the benefits explained herein. The SCS waveform illustrated in FIG. 8B can be referred to as a spline waveform shape and/or smooth waveform shape instead of the square wave or sharp corner shapes illustrated in FIG. 8A. FIG. 8C illustrates a table with example non-limiting pulse widths, pulse frequencies, amplitudes, and charge per pulse values for each of the conventional, burst, high frequency, and curved SCS waveforms. As provided in the table, the charge per pulse value for the curved SCS waveform illustrated in FIG. 8B can be much greater than, and even orders of magnitude greater than that of the other SCS waveforms.

Figure 9:
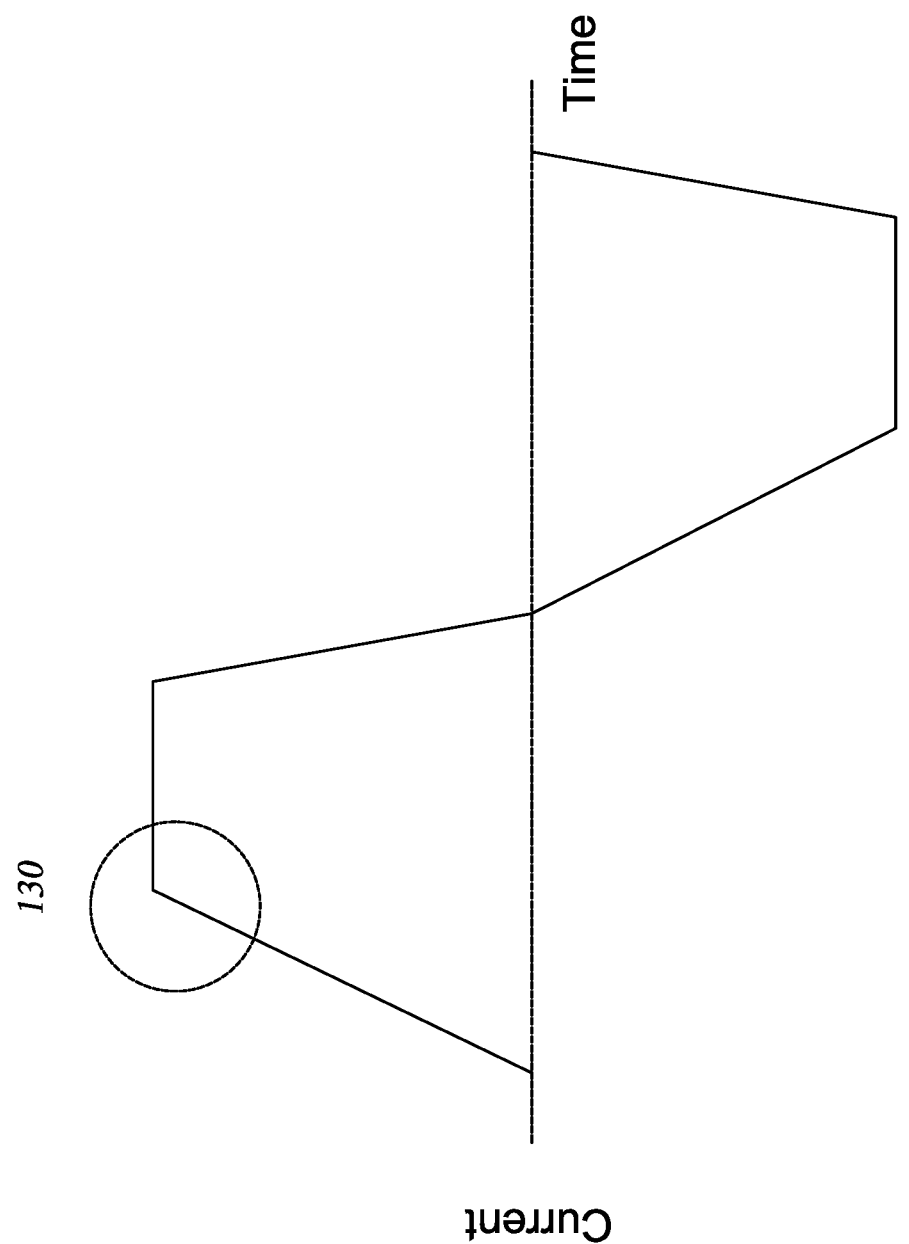
FIG. 9 illustrates an example waveform.

FIG. 9 illustrates a SCS waveform with sharp corners or angles. In some embodiments, sharp edges on stimulation waveforms can cause undesired responses. For example, the circled regions 130 indicate where undesirable motor activity (hind-leg contractions in animal models) have been observed. Rounding the sharp angles, corners, or edges can advantageously increase the amplitude that can be driven prior to generating motor activity.

Figure 10:
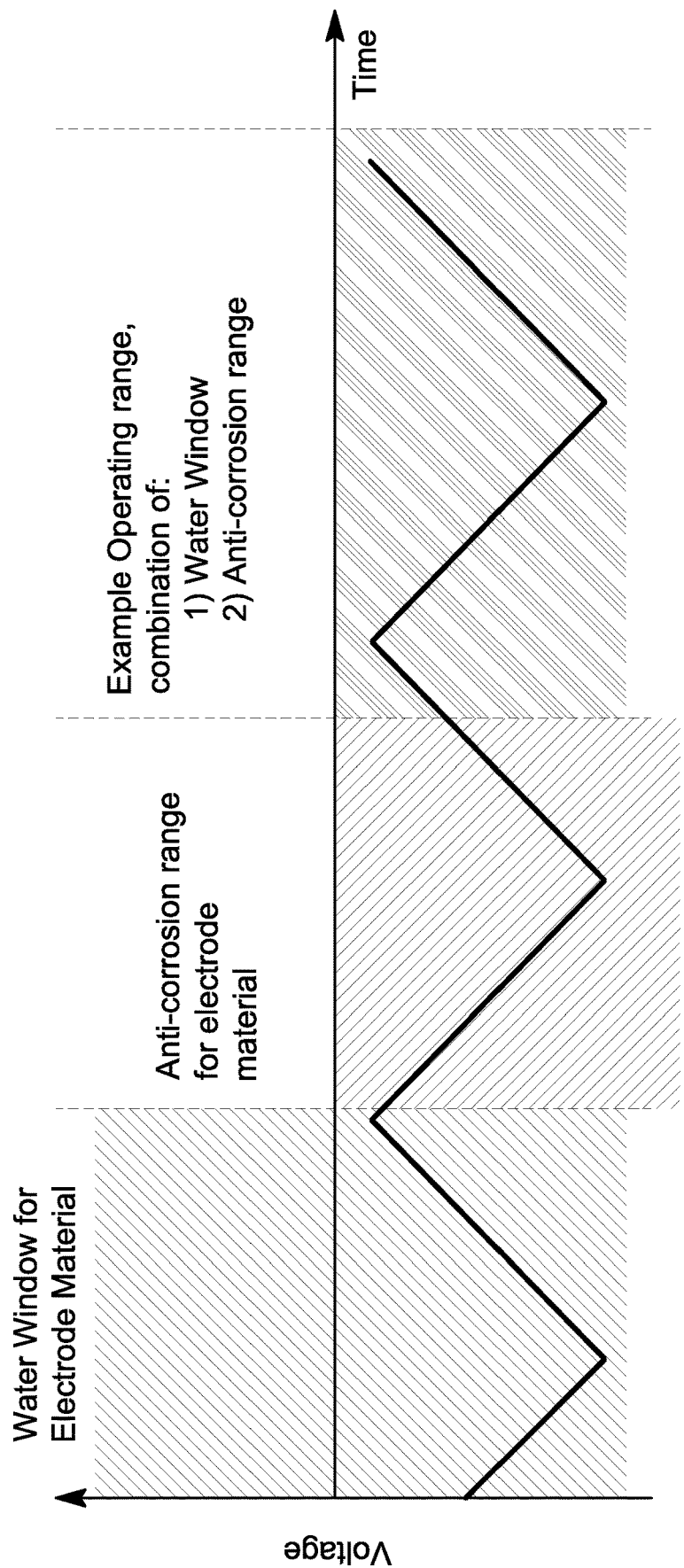
FIG. 10 illustrates an example waveform of an electrode operated in ranges to limit chemical by products and protect the electrode from undesirable reactions.

FIG. 10 illustrates an example graph representative of operating electrodes in favorable operating voltage ranges to limit, which can be irreversible, byproduct formation (e.g., chemical byproducts) and promote electrode longevity, which can include protecting the electrode from undesirable reactions (e.g. corrosion). The graph shows voltage over time with a water window for electrode material, anti-corrosion range for electrode material, and an example operating range for a combination of water window and anti-corrosion ranges.

Figure 11:
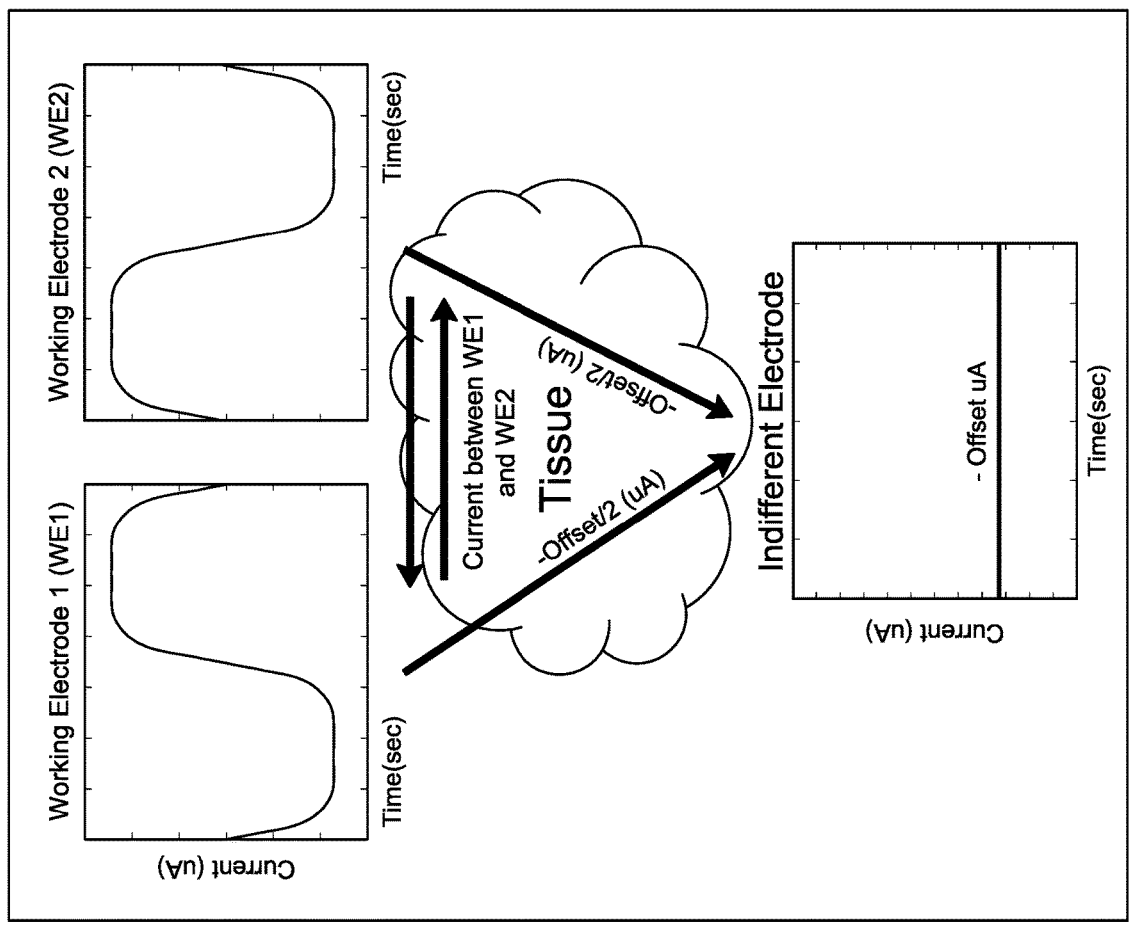
FIG. 11 illustrates an example bipolar operation with bias (or offset) current.

FIG. 11 illustrates an example bipolar operation with bias (offset) current. In a bipolar configuration, balanced low frequency stimulation current is conducted between two working electrodes (WE1, WE2). An offset current is added to each WE electrode and is absorbed by the indifferent electrode, which can be either a surface or implanted transcutaneous electrode that can accommodate the opposite voltage of the working electrode. FIG. 11 shows a non-limiting example of the bipolar arrangement with even bias (offset) currents for each electrode and a constant DC bias (offset) current. In a monopolar arrangement, stimulation current is conducted between the working electrode (WE) and a counter or indifferent electrode (IE). The counter or indifferent electrode can be a surface or implanted electrode or transcutaneous electrode that can accommodate the opposite voltage of the working electrode. Stimulation current can include an ultra low frequency AC component and an offset current can be added such that the WE is biased in the correct voltage range.

In some embodiments, systems and methods as disclosed herein can be used or modified for use as part of alternating current stimulation systems, including but not limited to spinal cord stimulation (SCS) systems for treatment of chronic pain, such as for example the SENZA system by Nevro Corporation; the PRECISION systems including PRECISION PLUS and PRECISION SPECTRA by Boston Scientific Corporation, and the INTELLIS system from Medtronic PLC. As one example, systems and methods as disclosed herein can increase efficacy of an alternating current delivery system including delivering alternating current via an electrode and electrode lead to a target tissue of a patient utilizing a DC-offset waveform generated by a pulse generator and facilitated by a controller. The alternating frequency could be any desired frequency, including high frequency systems of about 10 kHz or higher, from about 1.5 kHz to about 100 kHz, from about 1.5 kHz to about 50 kHz, from about 3 kHz to about 20 kHz, from about 3 kHz to about 15 kHz, from about 5 kHz to about 15 kHz, or from about 3 kHz to about 10 kHz, or other ranges incorporating any two of the aforementioned values. The electrode and/or electrode lead can include one or more of: high density charge materials, a SINE electrode, and/or a silver-silver chloride material. Such systems and methods can in some cases advantageously increase the excitability of target neurons, thereby decreasing thresholds and widening the therapeutic window of the target tissue stimulation.

The foregoing description and examples has been set forth to illustrate the disclosure according to various embodiments and are not intended as being unduly limiting. The headings provided herein are for organizational purposes only and should not be used to limit embodiments. Each of the disclosed aspects and examples of the present disclosure may be considered individually or in combination with other aspects, examples, and variations of the disclosure. In addition, unless otherwise specified, none of the steps of the methods of the present disclosure are confined to any particular order of performance. References cited herein are incorporated by reference in their entirety.

While the methods and devices described herein may be susceptible to various modifications and alternative forms, specific examples thereof have been shown in the drawings and are herein described in detail. It should be understood, however, that the embodiments disclosed should cover modifications, equivalents, and alternatives falling within the spirit and scope of the various embodiments described herein and the appended claims.

Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some examples, acts or events can be performed concurrently, e.g., through multi-threaded processing, interrupt processing, or multiple processors or processor cores or on other parallel architectures, rather than sequentially.

The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed.

The various illustrative logical blocks, modules, processes, methods, and algorithms described in connection with the embodiments disclosed herein can be implemented as electronic hardware, computer software, or combinations of both. To clearly illustrate this interchangeability of hardware and software, various illustrative components, blocks, modules, operations, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The blocks, operations, or steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, an optical disc (e.g., CD-ROM or DVD), or any other form of volatile or non-volatile computer-readable storage medium known in the art. A storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that some examples include, while other examples do not include, certain features, elements, and/or states. Thus, such conditional language is not generally intended to imply that features, elements, blocks, and/or states are in any way required for one or more examples or that one or more examples necessarily include logic for deciding, with or without author input or prompting, whether these features, elements and/or states are included or are to be performed in any particular embodiment.

The methods disclosed herein may include certain actions taken by a practitioner; however, the methods can also include any third-party instruction of those actions, either expressly or by implication. For example, actions such as "positioning an electrode" include "instructing positioning of an electrode."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 hour" includes "1 hour." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure. The phrase "at least one of" is intended to require at least one item from the subsequent listing, not one type of each item from each item in the subsequent listing. For example, "at least one of A, B, and C" can include A, B, C, A and B, A and C, B and C, or A, B, and C.

What is claimed is:

1. A system for electrically modulating tissue, comprising:
   a current generator;
   at least one implantable working electrode, the at least one implantable working electrode configured to be in electrical communication with the current generator;
   at least one indifferent electrode; and
   a controller configured to signal the current generator to:
      generate a set of currents with a set of initial polarities to be delivered to the working electrodes;
   wherein the at least one indifferent electrode absorbs a bias current which is equal in magnitude and opposite in polarity to a summation of the set of currents, and
   wherein the set of currents comprise ultra low frequency currents.

2. The system of claim 1, wherein the ultra low frequency currents are less than about 1 Hz.

3. The system of claim 1, wherein the ultra low frequency currents are less than about 0.1 Hz.

4. The system of claim 1, wherein the ultra low frequency currents are less than about 0.01 Hz.

5. A system for electrically modulating tissue, comprising:
   a current generator;
   at least one implantable working electrode, the at least one implantable working electrode configured to be in electrical communication with the current generator;
   at least one indifferent electrode; and
   a controller configured to signal the current generator to:
      generate a set of currents with a set of initial polarities to be delivered to the working electrodes; and
      wherein the at least one indifferent electrode absorbs a bias current which is equal in magnitude and opposite in polarity to a summation of the set of currents.

6. The system of claim 5, wherein the set of currents is sufficient to modulate electrically excitable tissue.

7. The system of claim 5, wherein the at least one implantable working electrode comprises a high charge capacity material.

8. The system of claim 7, wherein the high charge capacity material comprises tantalum coated with titanium nitride.

9. The system of claim 5, wherein the bias current operates in an anodic polarity.

10. The system of claim 5, wherein the bias current operates in a cathodic polarity.

11. The system of claim 5, wherein the set of currents are configured to generate the bias current that biases the working electrode voltages cathodically.

12. The system of claim 5, wherein the set of currents is configured to generate the bias current that biases the working electrode voltages anodically.

13. The system of claim 5, wherein the set of currents are configured to generate the bias current that biases the indifferent electrode voltages cathodically.

14. The system of claim 5, wherein the set of currents is configured to generate the bias current that biases the indifferent electrode voltages anodically.

15. The system of claim 5, comprising at least two working electrodes.

16. The system of claim 5, wherein the initial polarity of at least one working electrode is cathodic.

17. The system of claim 5, wherein the initial polarity of at least one working electrode is anodic.

18. The system of claim 5, wherein the indifferent electrode is a skin surface electrode.

19. The system of claim 5, wherein the indifferent electrode is a transcutaneous electrode or an implanted electrode.

20. The system of claim 5, wherein the indifferent electrode comprises titanium.

* * * * *